(12) United States Patent
Chen et al.

(10) Patent No.: US 11,860,121 B2
(45) Date of Patent: Jan. 2, 2024

(54) INTEGRATED CIRCUIT WITH BIOFETS

(71) Applicant: TAIWAN SEMICONDUCTOR MANUFACTURING CO., LTD., Hsinchu (TW)

(72) Inventors: Tung-Tsun Chen, Hsinchu (TW); Yi-Hsing Hsiao, Hsinchu (TW); Jui-Cheng Huang, Hsinchu (TW); Yu-Jie Huang, Kaohsiung (TW)

(73) Assignee: TAIWAN SEMICONDUCTOR MANUFACTURING CO., LTD., Hsinchu (TW)

( * ) Notice: Subject to any disclaimer, the term of this patent is extended or adjusted under 35 U.S.C. 154(b) by 0 days.

(21) Appl. No.: 17/884,382

(22) Filed: Aug. 9, 2022

(65) Prior Publication Data

US 2022/0381729 A1 Dec. 1, 2022

Related U.S. Application Data

(62) Division of application No. 17/007,973, filed on Aug. 31, 2020.

(51) Int. Cl.
*G01N 27/414* (2006.01)
*G01N 33/569* (2006.01)
*H01L 21/762* (2006.01)

(52) U.S. Cl.
CPC ..... *G01N 27/4148* (2013.01); *G01N 27/4145* (2013.01); *G01N 33/56966* (2013.01); *H01L 21/76251* (2013.01)

(58) Field of Classification Search
CPC .................. G01N 27/4148; G01N 27/4145
See application file for complete search history.

(56) References Cited

U.S. PATENT DOCUMENTS

| 6,471,689 B1 | 10/2002 | Joseph et al. |
| 8,728,844 B1 | 5/2014 | Liu et al. |
| 9,366,647 B2 | 6/2016 | Chang et al. |
| 9,709,524 B2 | 7/2017 | Liu et al. |

(Continued)

FOREIGN PATENT DOCUMENTS

| CN | 104051512 A | 9/2014 |
| TW | 201508271 A | 3/2015 |
| WO | 2015040930 A1 | 3/2015 |

OTHER PUBLICATIONS

Queen's Medical Centre, "Sequence of Changes in Myocardial Infarction" University of Nottingham, School of Health Sciences, Cardiology Teaching Package, https://www.nottingham.ac.uk/nursing/practice/resources/cardiology/acs/changes.php; May 29, 2020.

(Continued)

*Primary Examiner* — Erik Kielin
(74) *Attorney, Agent, or Firm* — Maschoff Brennan

(57) ABSTRACT

An IC includes a source region and a drain region in a semiconductor layer. A channel region is between the source region and the drain region. A sensing well is on a back surface of the semiconductor layer and over the channel region. An interconnect structure is on a front surface of the semiconductor layer opposite the back surface of the semiconductor layer. A biosensing film lines the sensing well and contacts a bottom surface of the sensing well that is defined by the semiconductor layer. A coating of selective binding agent is over the biosensing film and configured to bind with a cardiac cell.

20 Claims, 24 Drawing Sheets

(56) References Cited

U.S. PATENT DOCUMENTS

| | | |
|---|---|---|
| 9,873,100 B2 | 1/2018 | Chen et al. |
| 10,139,364 B2 | 11/2018 | Liu et al. |
| 10,280,456 B2 | 5/2019 | Chang et al. |
| 10,393,695 B2 | 8/2019 | Liu et al. |
| 10,478,797 B2 | 11/2019 | Chen et al. |
| 2003/0091609 A1 | 5/2003 | Hendriks |
| 2012/0032235 A1 | 2/2012 | Bikumandla |
| 2014/0151755 A1 | 6/2014 | Liu et al. |
| 2014/0184196 A1 | 7/2014 | Lieber et al. |
| 2014/0194298 A1 | 7/2014 | Rothberg et al. |
| 2015/0069522 A1 | 3/2015 | Zhang |
| 2015/0097214 A1 | 4/2015 | Chen et al. |
| 2016/0074828 A1 | 3/2016 | Chen et al. |
| 2016/0334362 A1 | 11/2016 | Liu et al. |
| 2017/0002315 A1 | 1/2017 | Urisu et al. |
| 2017/0227533 A1 | 8/2017 | Lin et al. |
| 2017/0315086 A1 | 11/2017 | Chen et al. |
| 2017/0343498 A1 | 11/2017 | Kalnitsky et al. |
| 2018/0095073 A1 | 4/2018 | Hickman |
| 2018/0164246 A1 | 6/2018 | Chen et al. |
| 2018/0172627 A1 | 6/2018 | Chang et al. |
| 2019/0256910 A1 | 8/2019 | Chang et al. |
| 2020/0078760 A1 | 3/2020 | Chen et al. |
| 2020/0078761 A1 | 3/2020 | Chen et al. |
| 2020/0094215 A1 | 3/2020 | Chen et al. |
| 2020/0094216 A1 | 3/2020 | Chen et al. |
| 2021/0215683 A1 | 7/2021 | Yang et al. |

OTHER PUBLICATIONS

John A. Ryan, "Evolution of Cell Culture Surfaces", BioFiles, 2018 3.8, 21.

Grigoriy Ikonnikov and Eric Wong, "Action Potential of Cardiac Muscles", McMaster Pathophysiology Review, Oct. 7, 2013.

Grigoriy Ikonnikov and Eric Wong, "Cardiomyocyte Contractile Cycle", McMaster Pathophysiology Review, Oct. 7, 2013.

INTEGRATED CIRCUIT WITH BIOFETS

PRIORITY CLAIM AND CROSS-REFERENCE

The present application is a Divisional Application of U.S. application Ser. No. 17/007,973, filed Aug. 31, 2020, which is herein incorporated by reference in its entirety.

BACKGROUND

Biosensors are devices for sensing and detecting bio-entities, and typically operate on the basis of electronic, chemical, optical, or mechanical detection principles. Detection can be performed by detecting the bio-entities themselves, or through interaction and reaction between specified reactants and the bio-entities. Biosensors are widely used in different life-science applications, ranging from environmental monitoring and basic life science research to Point-of-Care (PoC) in-vitro molecular diagnostics.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

Figure 1:
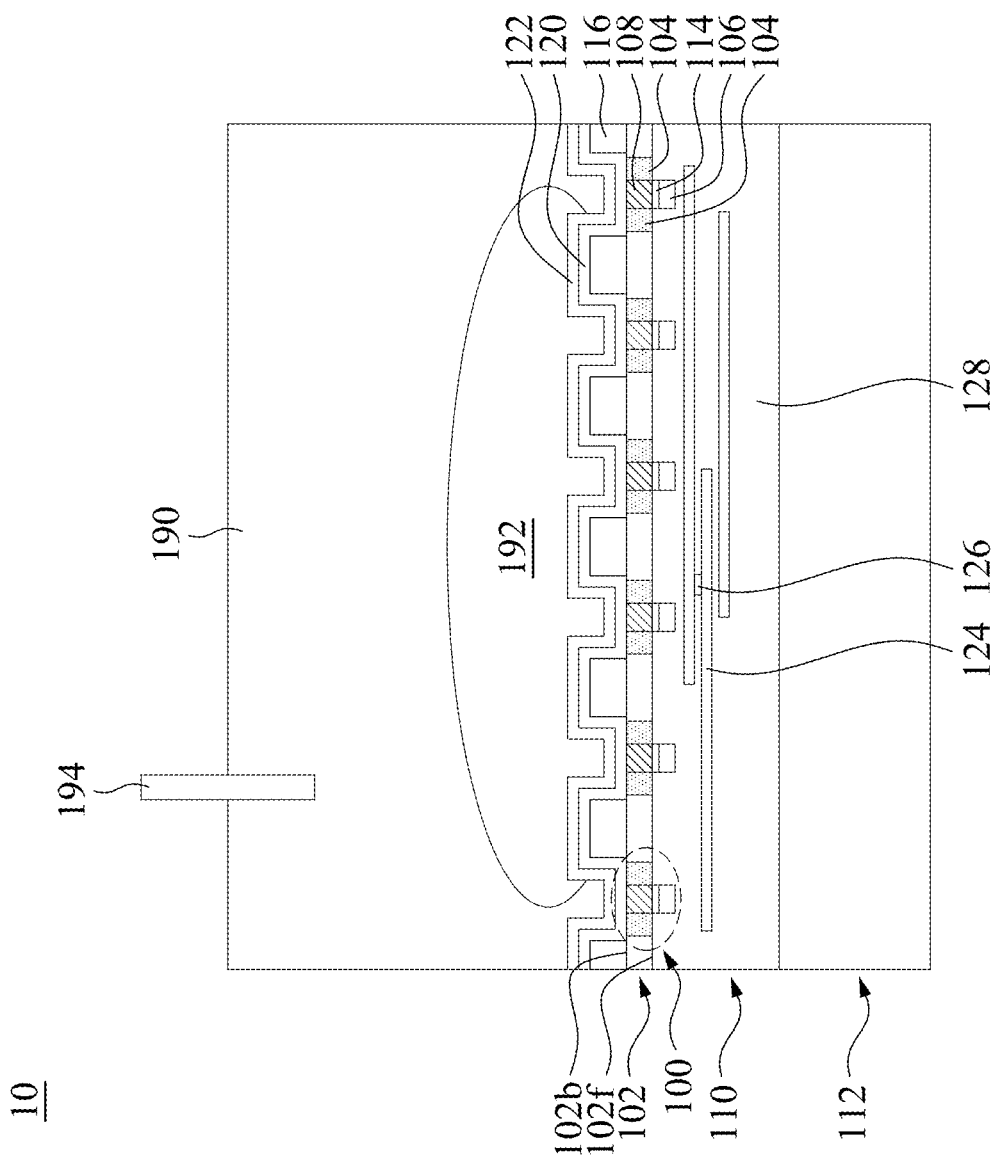
FIG. 1 illustrates a cross-sectional view of an example integrated circuit including an array of BioFETs in accordance with some embodiments of the present disclosure.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

One type of biosensor includes a semiconductor substrate that is covered by an isolation dielectric layer and that accommodates a biologically sensitive field-effect transistor (BioFET). One advantage of BioFETs is the prospect of label-free operation. Specifically, BioFETs enable the avoidance of costly and time-consuming labeling operations such as the labeling of analytes (e.g., cardiac cells) with, for instance, fluorescent or radioactive probes. The BioFET includes a source region and a drain region that are arranged within the semiconductor substrate and that define a channel region therebetween. Further, the BioFET includes a gate arranged under the semiconductor substrate, laterally between the source region and the drain region. The isolation dielectric layer includes a sensing well that exposes the semiconductor substrate, laterally between the source region and the drain region, and that is lined by a biosensing film. The biosensing film is configured to detect an impedance change, molecule charge and/or ion release resulting from bio-entities (e.g., cardiac cells), such that 2D electrical image profile of the bio-entities (e.g., cardiac cells) can be obtained and/or the bio-entities may be monitored.

FIG. 1 illustrates a cross-sectional view of an example integrated circuit 10 including an array of BioFETs 100 in accordance with some embodiments of the present disclosure. The BioFETs 100 each include a pair of source/drain regions 104 and, in some embodiments, a gate electrode 106. The source/drains regions 104 have a first conductivity type (i.e., doping type) and are arranged within an active semiconductor layer 102, respectively on opposite sides of a channel region 108 of the BioFET 100. The channel region 108 has a second conductivity type opposite the first conductivity type and is arranged in the active semiconductor layer 102, laterally between the source/drain regions 104. The first and second doping types may, for example, respectively be n-type and p-type, or vice versa. In some embodiments, the source/drain regions 104 and the channel region 108 are arranged within a doped well region of the active semiconductor layer 102 that has the second conductivity type, and/or are electrically coupled to a back-end-of-line (BEOL) interconnect structure 110 that is arranged over a carrier substrate 112.

Further, in some embodiments, the source/drain regions 104 and the channel region 108 extend from a front surface 102$f$ of the active semiconductor layer 102 to a back surface 102$b$ of the active semiconductor layer 102. Stated differently, the source/drain regions 104 and the channel region 108 can extend through the full thickness of the active semiconductor layer 102 to facilitate functioning of biosensing. The gate electrode 106 is arranged on the front surface 102$f$ of the active semiconductor layer 102, laterally between the source/drain regions 104, and is spaced from the front surface 102$f$ of the active semiconductor layer 102 by a gate dielectric layer 114. In some embodiments, the gate electrode 106 is electrically coupled to the BEOL interconnect structure 110 is metal, doped polysilicon, or a combination of the foregoing. In some embodiments, the BioFETs 100 may be separated from each other using shallow trench isolation regions (not shown) laterally surrounding each of the BioFETs 100.

Gate dielectric layer 114 includes, for example, silicon dioxide and/or a high-k gate dielectric material with a dielectric constant higher than that of silicon dioxide. Exemplary high-k gate dielectric materials include, but are not limited to, silicon nitride, silicon oxynitride, hafnium oxide ($HfO_2$), hafnium silicon oxide (HfSiO), hafnium silicon oxynitride (HfSiON), hafnium tantalum oxide (HfTaO), hafnium titanium oxide (HfTiO), hafnium zirconium oxide (HfZrO), metal oxides, metal nitrides, metal silicates, transition metal-oxides, transition metal-nitrides, transition metal-silicates, oxynitrides of metals, metal aluminates, zirconium silicate, zirconium aluminate, zirconium oxide, titanium oxide, aluminum oxide, hafnium dioxide-alumina ($HfO_2$—$Al_2O_3$) alloy, other suitable high-k dielectric materials, and/or combinations thereof. In some embodiments, the gate dielectric includes a stack of an interfacial dielectric material and a high-k dielectric material.

In some embodiments, the active semiconductor layer 102 may be a silicon substrate or wafer. Alternatively, the semiconductor layer 102 may include another elementary semiconductor, such as germanium (Ge); a compound semiconductor including silicon carbide (SiC), gallium arsenic (GaAs), gallium phosphide (GaP), indium phosphide (InP), indium arsenide (InAs), and/or indium antimonide (InSb); an alloy semiconductor including SiGe, GaAsP, AlInAs, AlGaAs, GaInAs, GaInP, and/or GaInAsP; or combinations thereof. In the depicted embodiments, the active semiconductor layer 102 is a semiconductor layer of a semiconductor-on-insulator (SOI) substrate (e.g., silicon layer). In some embodiments, the carrier substrate (interchangeably referred to as handle substrate as well) 112 may be, for example, a bulk semiconductor substrate, such as a bulk substrate of monocrystalline silicon.

An isolation dielectric layer 116 is arranged on the back surface 102$b$ of the active semiconductor layer 102, and includes a plurality of sensing wells 118 over corresponding channel regions 108 of BioFETs 100. The sensing wells 118 extend into the isolation dielectric layer 116 to proximate the channel regions 108 of BioFETs 100 and are at least partially lined by a biosensing film 120. Further, in some embodiments, the sensing wells 118 extend through the isolation dielectric layer 116 to expose the respective channel regions 108 of BioFETs 100. The isolation dielectric layer 116 may be, for example, silicon dioxide, a buried oxide (BOX) layer of a SOI substrate, some other dielectric, or a combination of the foregoing. In some specific embodiments, the active semiconductor layer 102 is a silicon layer of a SOI substrate, and the isolation dielectric layer 116 is a BOX layer of the SOI substrate.

The biosensing film 120 lines the sensing wells 118 and, in some embodiments, covers the entire isolation dielectric layer 116. The biosensing film 120 is operative to modulate the source to drain conductivity of each bioFET 100 when contacted by a fluid 190 having a suitable composition or carrying specific analytes. For example, the fluid 190 is an aqueous solution containing cardiac cells 192. Examples of materials for biosensing film 120 that provide the functionality of biosensing include $HfO_2$, $SiO_2$, $Si_3N_4$, $Al_2O_3$, and $Ta_2O_5$. An upper surface of the biosensing film 120 includes a coating of a selective binding agent 122. The selective binding agent 122 includes one or more biological materials having the property of selectively binding with the cardiac cells 192. If the cardiac cell 192 is stably bound on the upper surface of the biosensing film 120, the overall charge concentration at the biosensing film 120 can become sufficient to modulate the source to drain conductivity of BioFETs 100, thus improving the biosensing performance. Because the selective binding agent 122 has a greater binding ability (i.e., greater adhesion) to the cardiac cell 192 than that of the biosensing film 120, the biosensing performance can be improved as long as the selective binding agent 122 is coated on the biosensing film 120. In some embodiments, the selective binding agent 122 for selectively binding with the cardiac cell 192 includes, for example, collagen, laminin, fibronectin, and mucopolysaccharides, heparin sulfate, hyaluronidate, chondroitin sulfate, the like, or combinations thereof. The coating of the selective binding agent 122 is illustrated as a blanket layer covering the entire biosensing film 120 merely for the sake of clarity, but in practice the coating of the selective binding agent 122 is porous and thus does not cover the entire biosensing film 120, which allows the biosensing film 120 to be in contact with the cardiac-cell-containing fluid 190.

The sensor array of BioFETs 100 can use the biosensing film 120 to monitor beating of the cardiac cells 192 and/or generate 2D image profiles of the cardiac cells 192 by detecting impedance change, module charge and/or ion release. Take ion release detection for example, in operation a reference electrode 194 gives the cardiac-cell-containing solution 190 a voltage potential, then the biosensing film 120 becomes charged when brought in contact with the cardiac cell containing fluid 190 having a suitable ion concentration. Moreover, they can become sufficiently charged to switch the source/drain conductivity of bioFETs 100. In this way, the sensor array of bioFETs 100 has the biosensing film 120 functional to detect ion released from or captured on the cardiac cell 192 and/or ion released from or captured on the selective binding agent 122. In a similar manner, the sensor array of bioFETs 100 can detect molecule charge released from or captured on the cardiac cell 192 and/or charge released from or captured on the selective binding agent 122.

Figure 2:
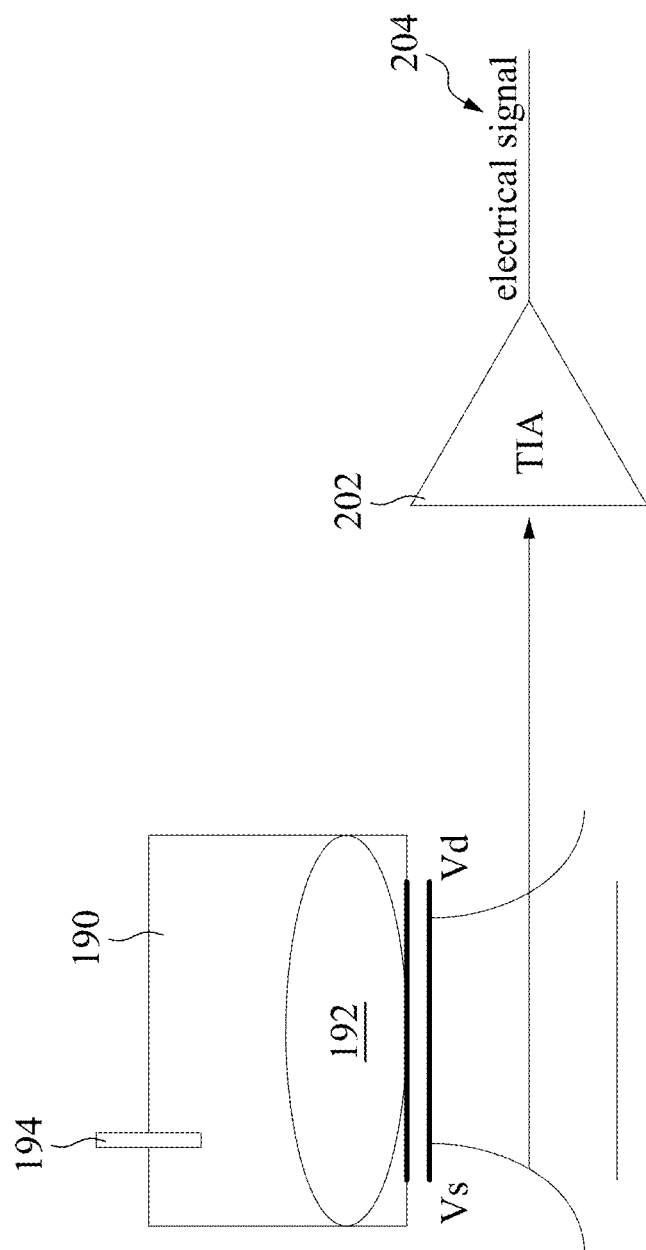
FIG. 2 illustrates an equivalent circuit that corresponds to a BioFET in accordance with some embodiments of the present disclosure.

In examples, the current between the source/drain regions 104 is measured, and the measured current (or a change in the measured current caused by the fluid 190 and/or the cardiac cell 192) is indicative of impedance change, molecule charge and/or ion release caused by the fluid 190 and/or the cardiac cell 192. Thus, in such examples, the detection mechanism is a conduction modulation of the transducer due to the binding of the cardiac cell 192 over the biosensing film 120. In other examples, one or more components (e.g., a trans-impedance amplifier) are used to translate the current or change of current induced by the fluid 190 and/or the cardiac cell 192 into another electrical signal, such as a measurable voltage. To illustrate this, reference is made to FIG. 2, which depicts a trans-impedance amplifier 202 used in generating an electrical signal 204, in accordance with some embodiments of the present disclosure. FIG. 2 illustrates an equivalent circuit that corresponds to a BioFET (e.g., BioFET 100 as illustrated in FIG. 1) and shows that a drain current induced by the fluid 190 and/or cardiac cell 192 on the upper surface of the biosensing film 120 is translated into the electrical signal 204 by the trans-impedance amplifier 202. The electrical signal 204 may include, for example, voltages (e.g., voltage signals) that can be measured.

In some embodiments, each of the BioFETs 100 may be controlled (i.e., turned on and turned off) by an access transistor. For example, as illustrated in to FIG. 3, a cross section of a BioFET 100 and an access transistor 300 is provided, according to some embodiments. The BioFET 100 includes source/drain regions 104, a channel region 108 laterally between the source/drain regions 104, a gate dielectric layer 114 over the channel region 108 and a gate electrode 106 over the gate dielectric layer 114, all of which are discussed previously with respect to FIG. 1 and thus are not repeated for the sake of brevity.

Figure 4:
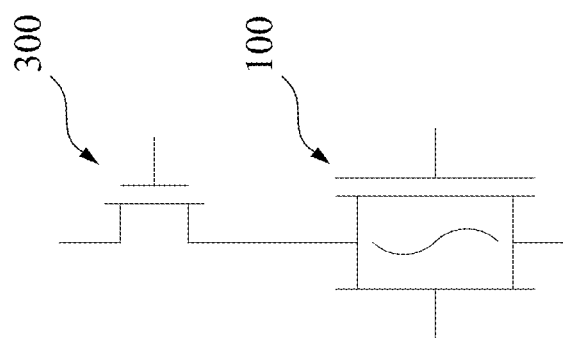
FIG. 4 illustrates an equivalent circuit that corresponds to the relationship between the BioFET and the access transistor as shown in FIG. 3.

The access transistor 300 is coupled to the BioFET 100, as illustrated in the circuit diagram of FIG. 4. The access transistor 300 similarly includes source/drain regions 304 formed in the semiconductor substrate 102, a channel region 308 laterally between the source/drain regions 304, a gate dielectric layer 314 over the channel region 308 and a gate electrode 306 over the gate dielectric layer 314. The source/drain regions 304 are doped regions having a conductivity type opposite the conductivity type of the channel region 308. For example, the source/drain regions 304 are of an n-type conductivity and the channel region 308 is of a p-type conductivity, or vice versa. In some embodiments, the gate electrode 306 of the access transistor 300 has a same material composition as the gate electrode 106 of the BioFET 100 and is formed simultaneously with the gate electrode 106. For example, the gate electrode 306 may be metal, doped polysilicon, or a combination of the foregoing. In some embodiments, the gate dielectric layer 314 has a same material composition as the gate dielectric layer 114 and is formed simultaneously with the gate dielectric layer 114, and thus example materials of the gate dielectric layer 314 are not repeated for the sake of brevity.

The access transistor 300 is similar with the BioFET 100, except that the channel region 308 and/or the source/drain regions 304 of the access transistor 300 are separated from the biosensing film 120 by the isolation dielectric layer 116.

In this way, operation of the access transistor 300 is not affected by the fluid 190 and/or the cardiac cell 192.

Figure 3:
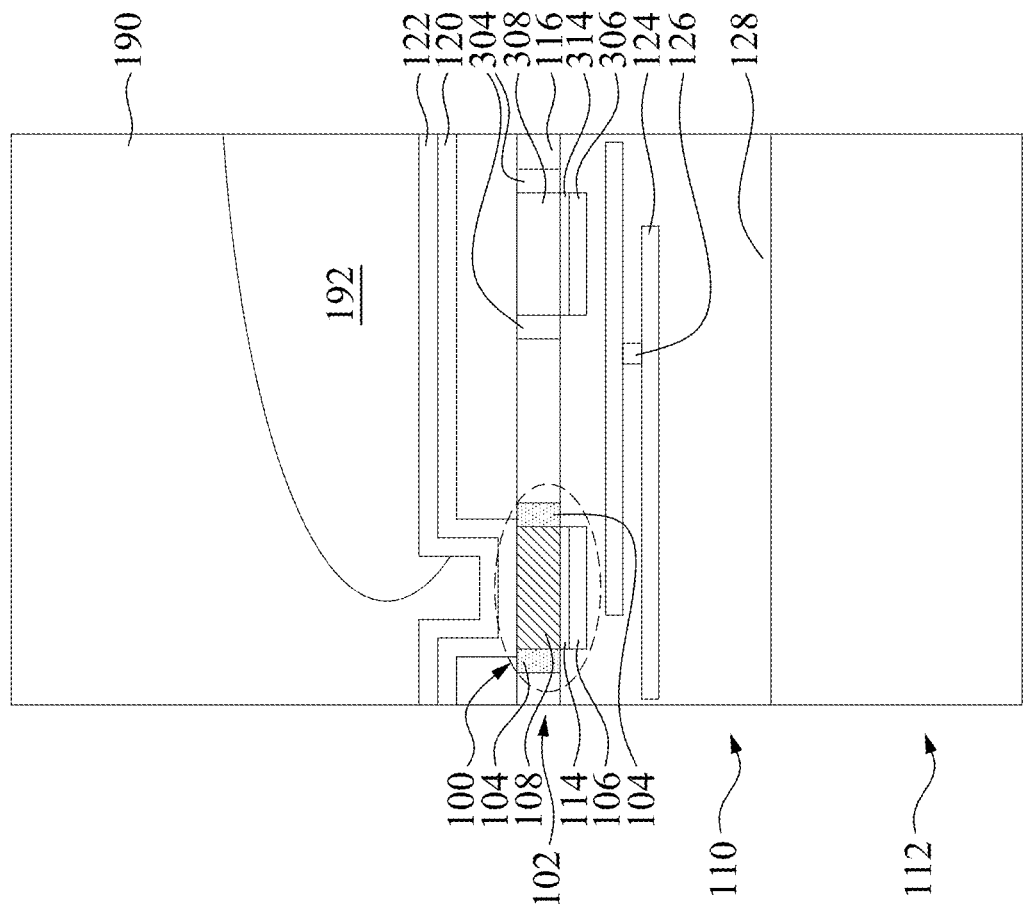
FIG. 3 illustrates a cross-sectional view of a BioFET and an access transistor for the BioFET in accordance with some embodiments of the present disclosure.

FIG. 4 illustrates an equivalent circuit that corresponds to the relationship between the BioFET 100 and the access transistor 300 as shown in FIG. 3. As illustrated in FIG. 4, the access transistor 300 serves as a switching device coupled to source/drain terminal of the BioFET 100, and thus the access transistor 300 can turn on the BioFET 100 to initiate detecting and/or monitoring the cardiac cell, and can also turn off the BioFET 100 to stop detecting and/or monitoring the cardiac cell.

Figure 5:
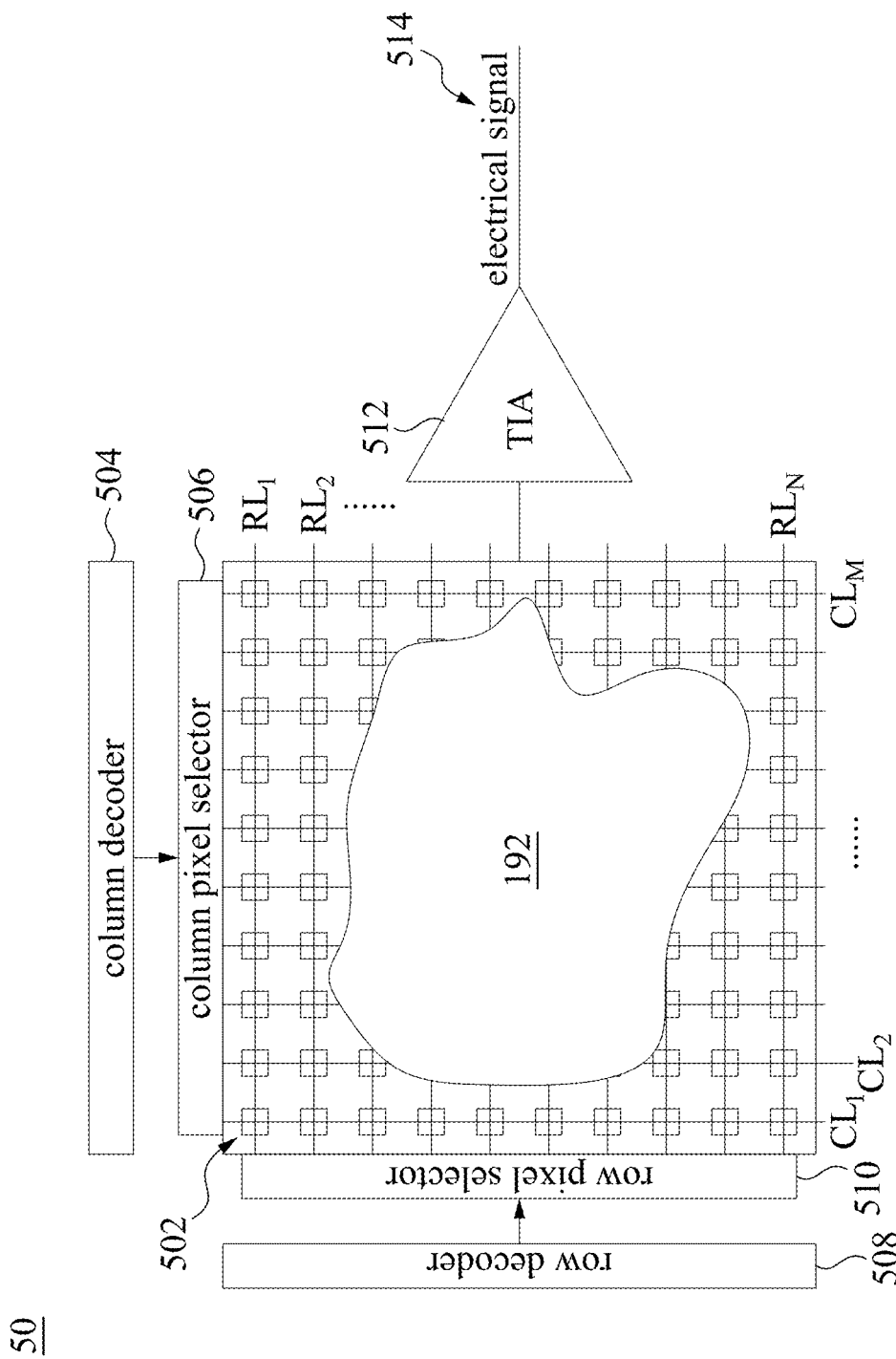
FIG. 5 is a functional block diagram of an integrated circuit in accordance some embodiments of the present disclosure.

FIG. 5 is a functional block diagram of an integrated circuit 50 in accordance some embodiments of the present disclosure. The integrated circuit 50 includes a sensing pixel array SA that includes sensing pixels 502 arranged into M columns and N rows. M and N are positive integers. In some embodiments, M ranges from 1 to 256. In some embodiments, N ranges from 1 to 256. The number of M and N are selected based on a normal size of a cardiac cell 192, which in turn allows for detecting/monitoring a single cardiac cell 192 using a single sensing pixel array SA. Each sensing pixel 502 of the array SA at least includes a BioFET (e.g., BioFET 100 as illustrated in FIGS. 3 and 4) and an access transistor (e.g., access transistor 300 as illustrated in FIGS. 3 and 4) coupled to the BioFET.

The integrated circuit 50 also includes a column decoder 504 coupled to the sensing pixel array SA via column lines $CL_1$-$CL_M$. The column decoder 504 decodes a column address of sensing pixels 502 selected to be accessed in a cardiac cell detection/monitor operation. The column decoder 504 then enables, via the column pixel selector 506, the column line corresponding to the decoded column address to permit access to the selected sensing pixels 502. The integrated circuit 50 also includes a row decoder 508 coupled to the sensing pixel array SA via row lines $RL_1$-$RL_N$. The row decoder decodes a row address of sensing pixels 502 selected to be accessed in a cardiac cell detection/monitor operation. The row decoder 508 then enables, via the row pixel selector 510, the row line corresponding to the decoded row address to permit reading out biosensing measurements from the selected sensing pixels 502. In some embodiments, the integrated circuit 50 further includes one or more trans-impedance amplifiers 512 configured to receive readout biosensing measurements from an output of the row decoder 508 and generate an electrical signal based on the readout biosensing measurements of the selected sensing pixels 502. By way of example and not limitation, the readout biosensing measurements of selected sensing pixels 502 include drain currents of BioFETs of the selected sensing pixels 502 and can be translated into electric signals 514 by the trans-impedance amplifier 512. The electric signals 514 may include, for example, voltages (e.g., voltage signals).

Figure 6:
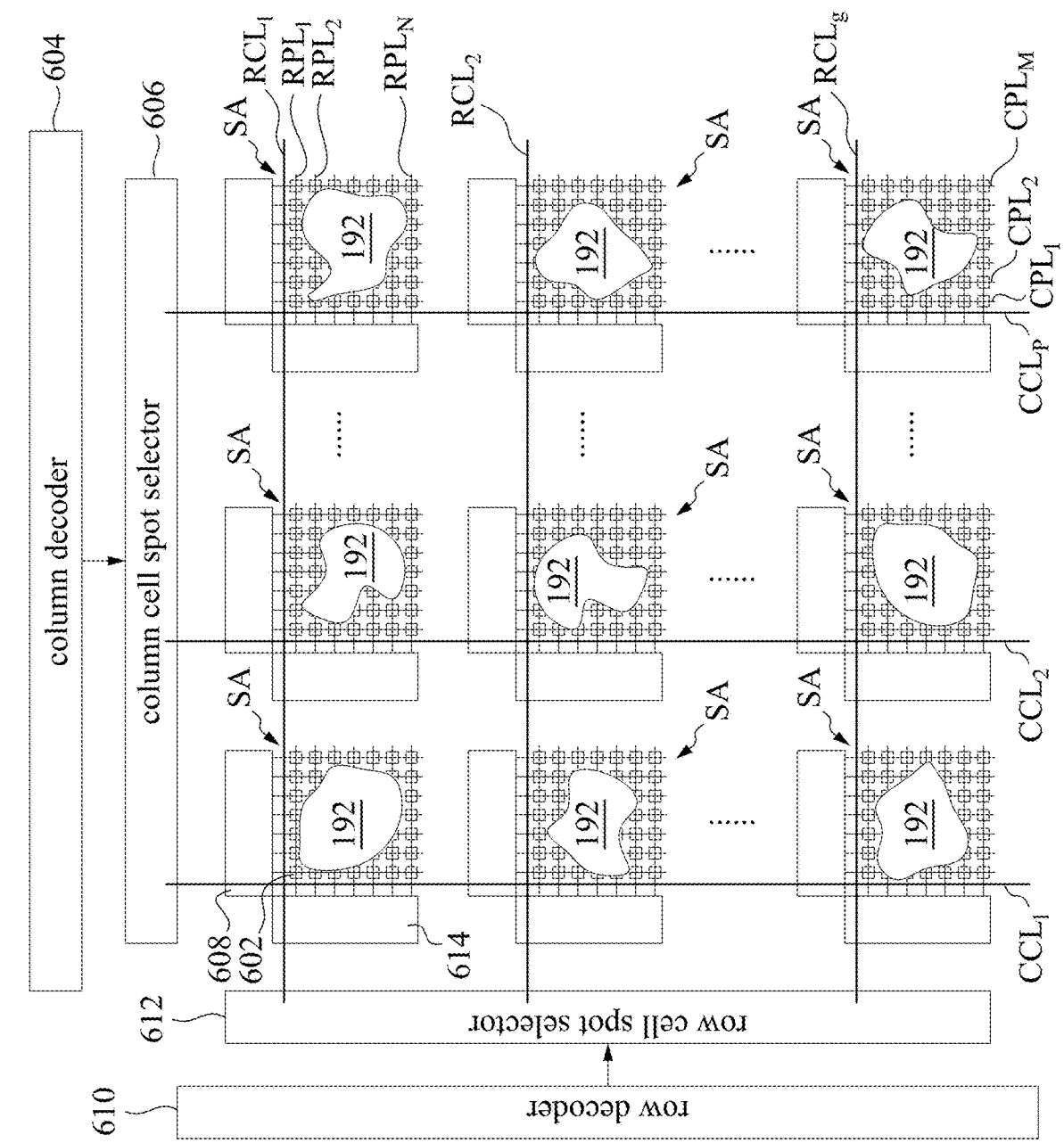
FIG. 6 is a functional block diagram of an example integrated circuit that is designed to detect/monitor multiple cardiac cells in accordance some embodiments of the present disclosure.

The integrated circuit 50 allows for detecting/monitoring a single cardiac cell. However, in some embodiments, multiple cardiac cells can be detected/monitored using an integrated circuit. FIG. 6 is a functional block diagram of an example integrated circuit 60 that is designed to detect/monitor multiple cardiac cells 192 in accordance some embodiments of the present disclosure. The integrated circuit 60 includes multiple sensing pixel arrays SA. Each sensing pixel arrays SA includes sensing pixels 602 each including a BioFET (e.g., BioFET 100 as illustrated in FIGS. 3 and 4) and an access transistor (e.g., access transistor 300 as illustrated in FIGS. 3 and 4) coupled to the BioFET.

The sensing pixels 602 in each sensing pixel array SA are arranged into M columns and N rows. M and N are positive integers. In some embodiments, both M and N range from 1 to 256. The number of M and N are selected based on a normal size of a cardiac cell 192, which in turn allows for detecting/monitoring a single cardiac cell 192 using a single sensing pixel array SA. Therefore, the integrated circuit 60 having multiple sensing pixel arrays SA can detect and/or monitor multiple cardiac cells 192. The sensing pixel arrays SA are arranged into P columns and Q rows. P and Q are positive integers. In some embodiments, P is less than M, and Q is less than N. In some other embodiments, P is greater than M, and Q is greater than N. The number of P and Q are selected depending on a desired number of cardiac cells to be detected and/or monitored.

The integrated circuit 60 includes a column decoder 604 coupled to the sensing pixel arrays SA via column cell spot lines $CCL_1$-$CCL_p$ and to the sensing pixels 602 via column pixel lines $CPL_1$-$CPL_M$. The column decoder 604 decodes a column cell spot address of sensing pixel arrays SA and a column pixel address of sensing pixels 602 of the selected sensing pixel array SA. The column decoder 604 then enables, via the column cell spot selector 606, the column cell spot line corresponding to the decoded column cell spot address, to permit access to the selected sensing pixel arrays SA. The column decoder 604 then enables, via the column pixel selector 608, the column pixel line corresponding to the decoded column pixel address, so as to permit access to the selected sensing pixels 602 of the selected sensing pixel arrays SA.

The integrated circuit 60 includes a row decoder 610 coupled to the sensing pixel arrays SA via row cell spot lines $RCL_1$-$RCL_q$ and to the sensing pixels 602 via row pixel lines $RPL_1$-$RPL_N$. The row decoder 610 decodes a row cell spot address of sensing pixel arrays SA and a row pixel address of sensing pixels 602 of the selected sensing pixel array SA. The row decoder 610 then enables, via the row cell spot selector 612, the row cell spot line corresponding to the decoded row cell spot address. The row decoder 610 then enables, via the row pixel selector 614, the row pixel line corresponding to the decoded row pixel address, so as to permit reading out biosensing measurements from the selected sensing pixels 602 of the selected sensing pixel arrays SA.

Figure 7:
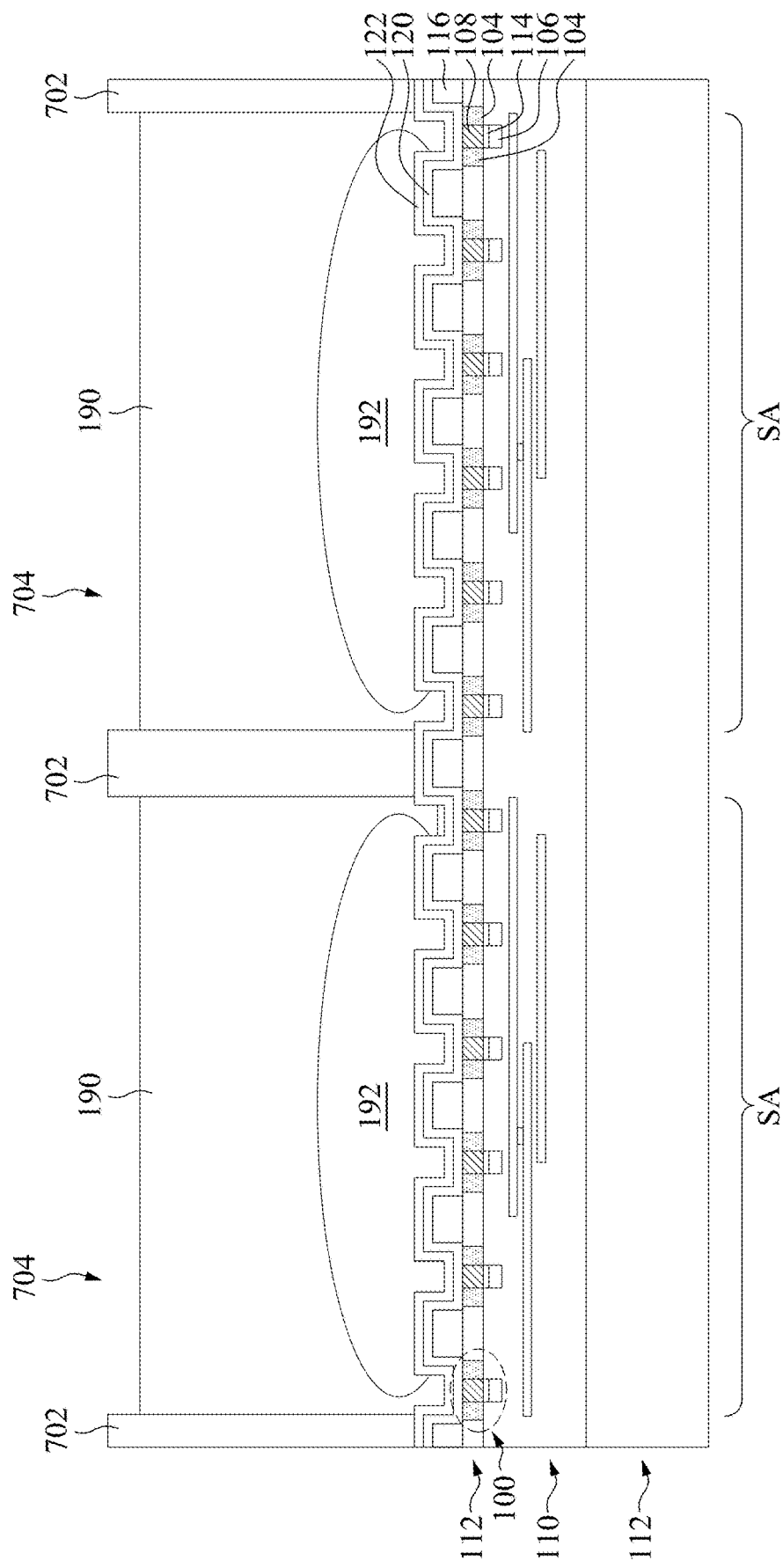
FIG. 7 illustrates an example cross-sectional view of a partial region of the integrated circuit of FIG. 6.

FIG. 7 illustrates an example cross-sectional view of a partial region of the integrated circuit 60 of FIG. 6. FIG. 7 illustrates two neighboring sensing pixel array SA spaced apart by one or more fluid channel walls 702. The fluid channel walls 702 laterally define fluid containment regions 704 over the respective sensing pixel arrays SA. Each sensing pixel array SA includes BioFETs 100 of sensing pixels. The fluid containment region 704 can be a well or a length of channel bound by fluid channel walls 702. The fluid channel walls 702 can be formed of waterproof material(s). In some embodiments, the fluid channel walls 702 are an elastomer. In some of these embodiments, the elastomer of polydimethylsiloxane (PDMS). In some embodiments, fluid containment regions 704 are capped to provide closed channels or reservoirs. Spacing between the fluid channel walls 702 are selected such that a single fluid containment region 704's size matches with a normal size of a cardiac cell 192. By way of example, the fluid containment region 704 has a width in a range from about 10 um to about 300 um. If the width of the fluid containment region 704 is less than about 10 um, the fluid containment region 704 may be too narrow to accommodate a single cardiac cell 192. If the width of the fluid containment region 704 is greater than about 300 um, the fluid containment region 704 may accommodate multiple cardiac cells 193. The BioFETs 100 are discussed previously with respect to FIG. 1 and thus are not repeated for the sake of brevity.

Figure 8:
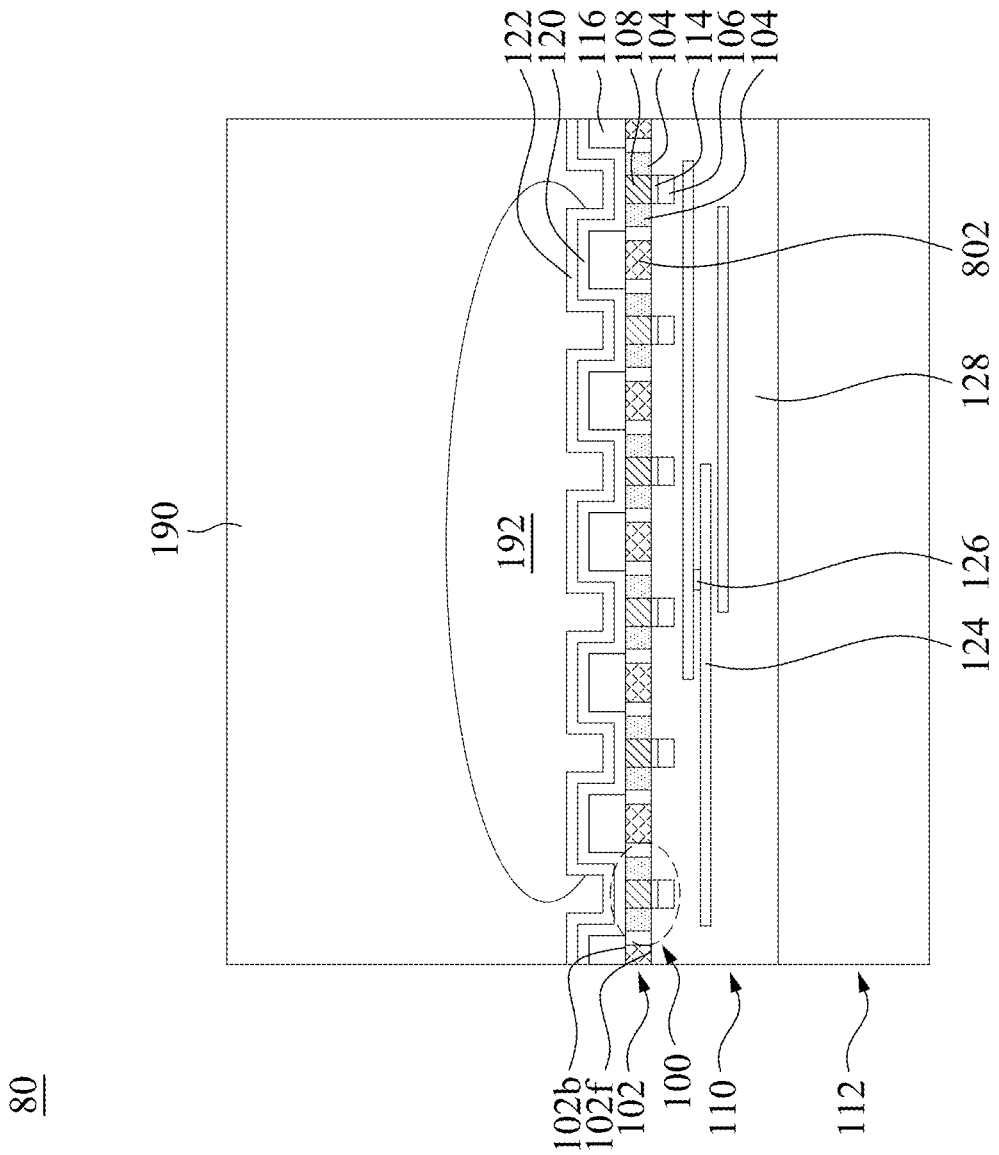
FIG. 8 illustrates a cross-sectional view of an example integrated circuit including an array of BioFETs in accordance with some embodiments of the present disclosure.

FIG. 8 illustrates a cross-sectional view of an example integrated circuit 80 including an array of BioFETs 100 in accordance with some embodiments of the present disclosure. The integrated circuit 80 is similar to the integrated circuit 10 of FIG. 1, except that the integrated circuit 80 includes additional heaters 802. In some embodiments, the heaters 802 are doped regions in the active semiconductor layer 102. In some embodiments, the heaters 802 are formed together with (i.e., simultaneously with) the source/drain regions 104, and thus have the same dopant type and dopant concentration profile as the source/drain regions 104. Different from the source/drain regions 104, the heaters 802 in the active semiconductor layer 102 are separated from the channel regions 104 by, for example, shallow trench isolation (STI), and thus the voltage applied to the heaters 802 does not affect functionality of the BioFETs 100. With the heaters 802, the fluid 190 and/or the cardiac cell 192 can be heated to enhance the detection and/or monitoring of the cardiac cell 192. In some embodiments, the heaters 802 are operated in response to a temperature measurement from a temperature-sensing device (not shown in FIG. 8), as discussed below.

Figure 9:
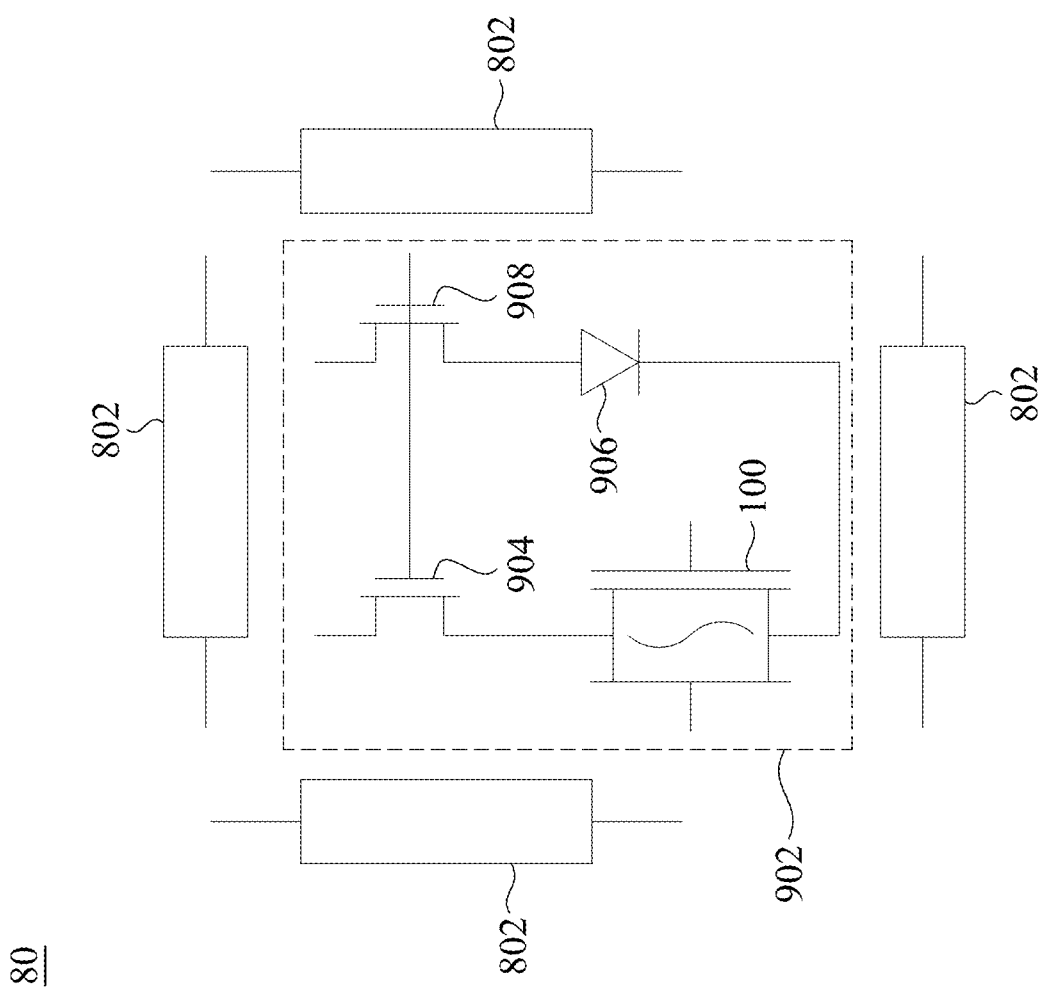
FIG. 9 is a circuit diagram of a BioFET and its surrounding heaters of the integrated circuit in accordance with some embodiments.

FIG. 9 is a circuit diagram of a BioFET 100 and its surrounding heaters 802 of the integrated circuit 80 in accordance with some embodiments. The integrated circuit 80 includes a sensing pixel 902 having a BioFET 100, a first switching device 904, a temperature-sensing device 906, and a second switching device 908. The first switching device 904 is coupled between a first end of the BioFET 100 and a corresponding row line (e.g., one of the row lines $RL_1$-$RL_N$ as illustrated in FIG. 5). The second switching device 908 is coupled between a first end of the temperature-sensing device 906 and a corresponding signal path for reading out the temperature measurement of the temperature-sensing device 906. The first switching device 904 and the second switching device 908 are N-type transistors having gates coupled with a corresponding column line (e.g., one of the column lines $CL_1$-$CL_M$ as illustrated in FIG. 5). A second end of the BioFET 100 and a second end of temperature-sensing device 906 are coupled together and configured to receive a reference voltage. In some embodiments, temperature-sensing device 906 includes a p-n diode formed in the active semiconductor layer 102 (as shown in FIG. 8). In some embodiments, the first switching device 904 or second switching device 908 is implemented by other types of switching devices, such as a transmission gate or a P-type transistor.

Temperature-sensing device 906 is configured to measure a temperature of the biosensing film of the BioFET 100 and then generate a temperature-sensing signal responsive to the measured temperature of the biosensing film. The heaters 802 are configured to adjust the temperature of the biosensing film of the BioFET 100, which in turn adjusts the temperature of the cardiac-cell-containing fluid and the cardiac cell over the BioFET 100. The temperature-sensing signal generated from the temperature-sensing device 906 can serve as feedback to control the heaters 802, which in turn promotes good temperature control and uniformity. By way of example and not limitation, when the measured temperature from the temperature-sensing device 906 is higher than an expected temperature range suitable for detecting and/or monitoring the cardiac cell 192, the heaters 802 are turned off; when the measured temperature from the temperature-sensing device 906 is lower than the expected temperature range, the heaters 802 are turned off.

Figure 10:
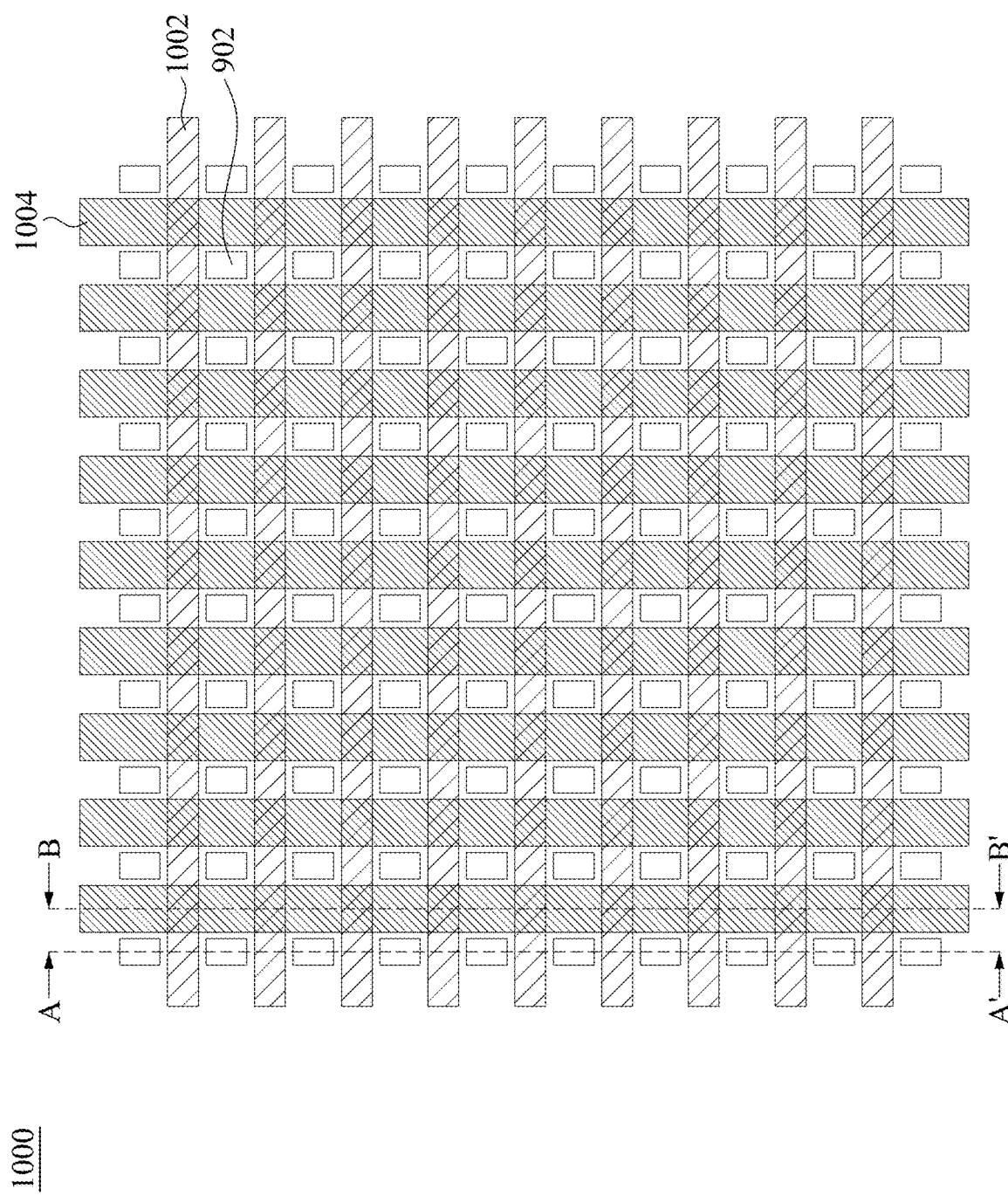
FIG. 10 is a layout diagram illustrating a configuration of sensing pixels and heaters in accordance with some embodiments of the present disclosure.

In some embodiments, as illustrated in FIG. 9, separate heaters 802 together surround four sides of the sensing pixel 902. However, in some other embodiments an integrated circuit has a different heater configuration, as illustrated in a layout diagram of FIG. 10. As shown in FIG. 10, the layout 1000 includes a plurality of first elongated heaters 1002 extending in a first direction, a plurality of second elongated heaters 1004 extending across the first elongated heaters 1002 in a second direction perpendicular to the first direction, and a plurality of sensing pixels 902 bound by the first elongated heaters 1002 and the second elongated heaters 1004. The sensing pixels 902 each include a BioFET 100, a temperature-sensing device 906, and first and second switching devices 904 and 908, as discussed previously with respect to FIG. 9.

Figure 11:
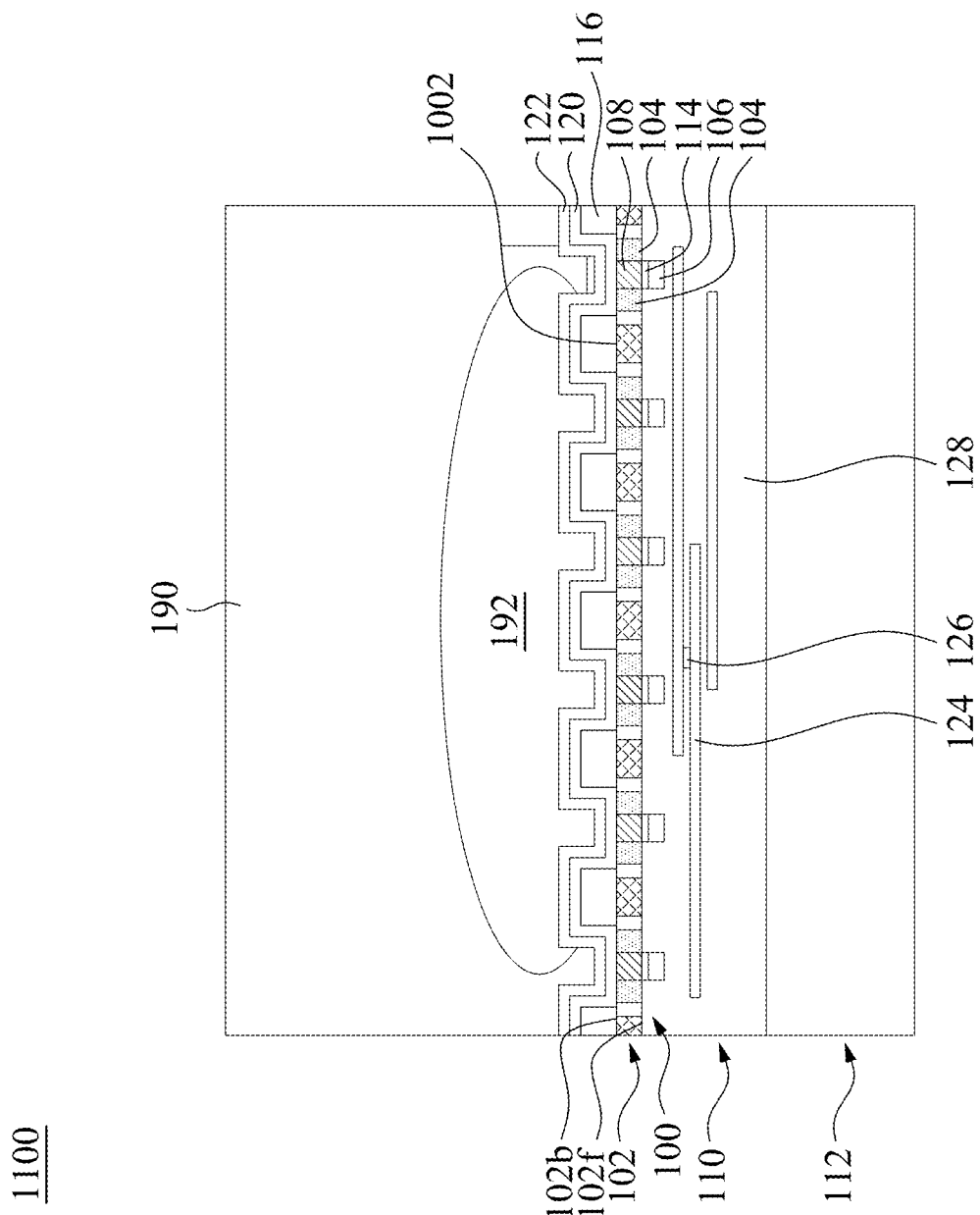
FIG. 11 is a cross-sectional view of an example integrated circuit having the layout of FIG. 10 taken along line A-A' of FIG. 10.
Figure 12:
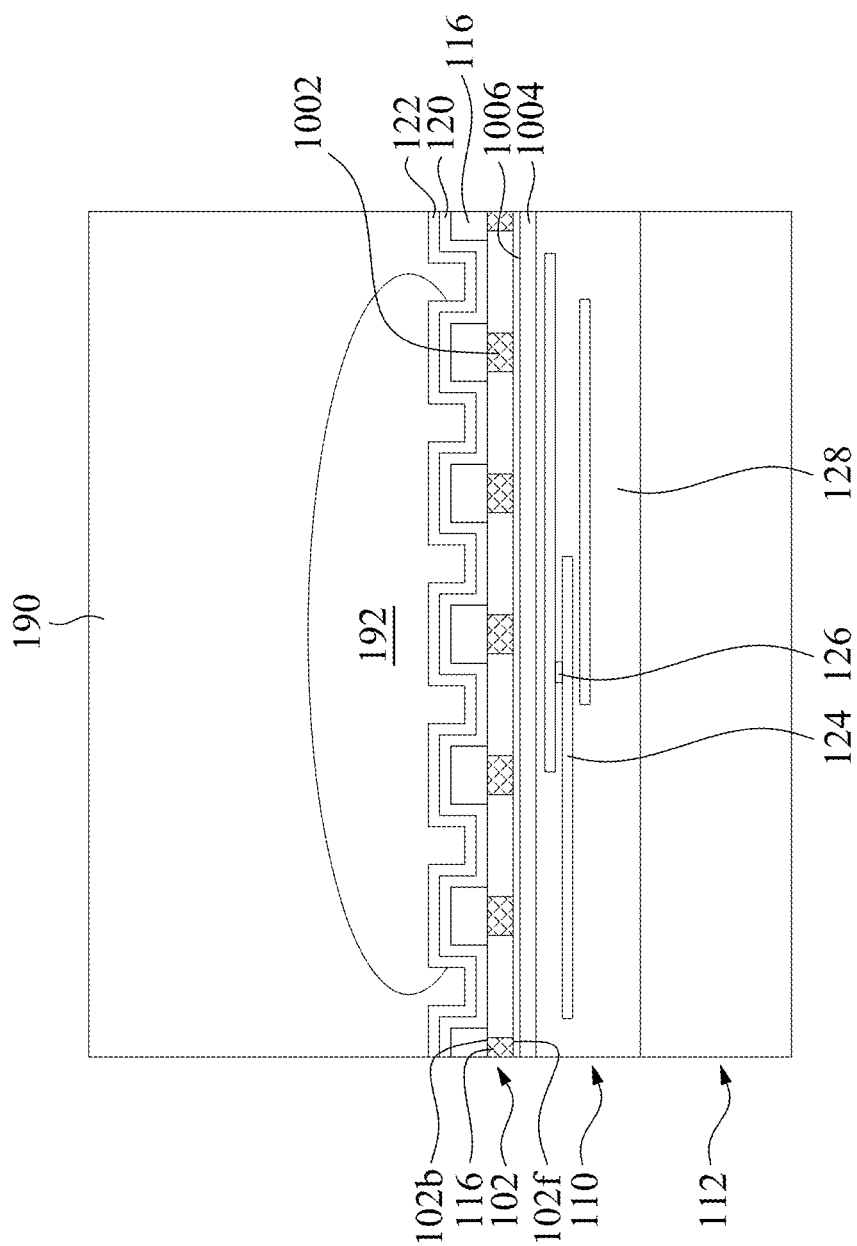
FIG. 12 is a cross-sectional view of an example integrated circuit having the layout of FIG. 10 taken along line B-B' of FIG. 10.

FIGS. 11 and 12 illustrate cross-sectional views of an example integrated circuit 1100 having the top view layout 1000 of FIG. 10 in accordance with some embodiments, wherein FIG. 11 is a cross-sectional view taken along line A-A' of FIG. 10, and FIG. 12 is a cross-sectional view taken along line B-B' of FIG. 10. As illustrated in FIGS. 11 and 12, the first elongated heaters 1002 are doped regions formed in the active semiconductor layer 102, and the second elongated heaters 1004 are doped polysilicon structure formed on the front surface 102f of the active semiconductor layer 102. In some embodiments where the gate electrodes 106 are polysilicon, the second elongated heaters 1004 are formed together with the polysilicon gates 106, and thus have the same thickness and material composition as the polysilicon gates 106. The first elongated heaters 1002 are thus interchangeably referred to as doped silicon heaters, and the second elongated heaters 1004 are thus interchangeably referred to as polysilicon heaters.

The polysilicon heaters 1004 are vertically spaced apart from the doped silicon heaters 1002 by a dielectric layer 1006, as illustrated in FIG. 12. In some embodiments, the dielectric layer 1006 is formed together with the gate dielectric layers 114 of the BioFETs 100, and thus the dielectric layer 1006 has the same thickness and material composition as the gate electric layers 114. By way of example and not limitation, the dielectric layer 1006 includes silicon dioxide, a high-k dielectric material with a dielectric constant higher than a dielectric constant of silicon dioxide or combinations thereof. In some embodiments, the doped silicon heaters 1002 and the polysilicon heaters 1004 non-overlap with BioFETs 100 of all sensing pixels 902 from a top view as illustrated in FIG. 10, and thus the doped silicon heaters 1002 and the polysilicon heaters 1004 do not affect the functionality of BioFETs 100.

Figure 13:
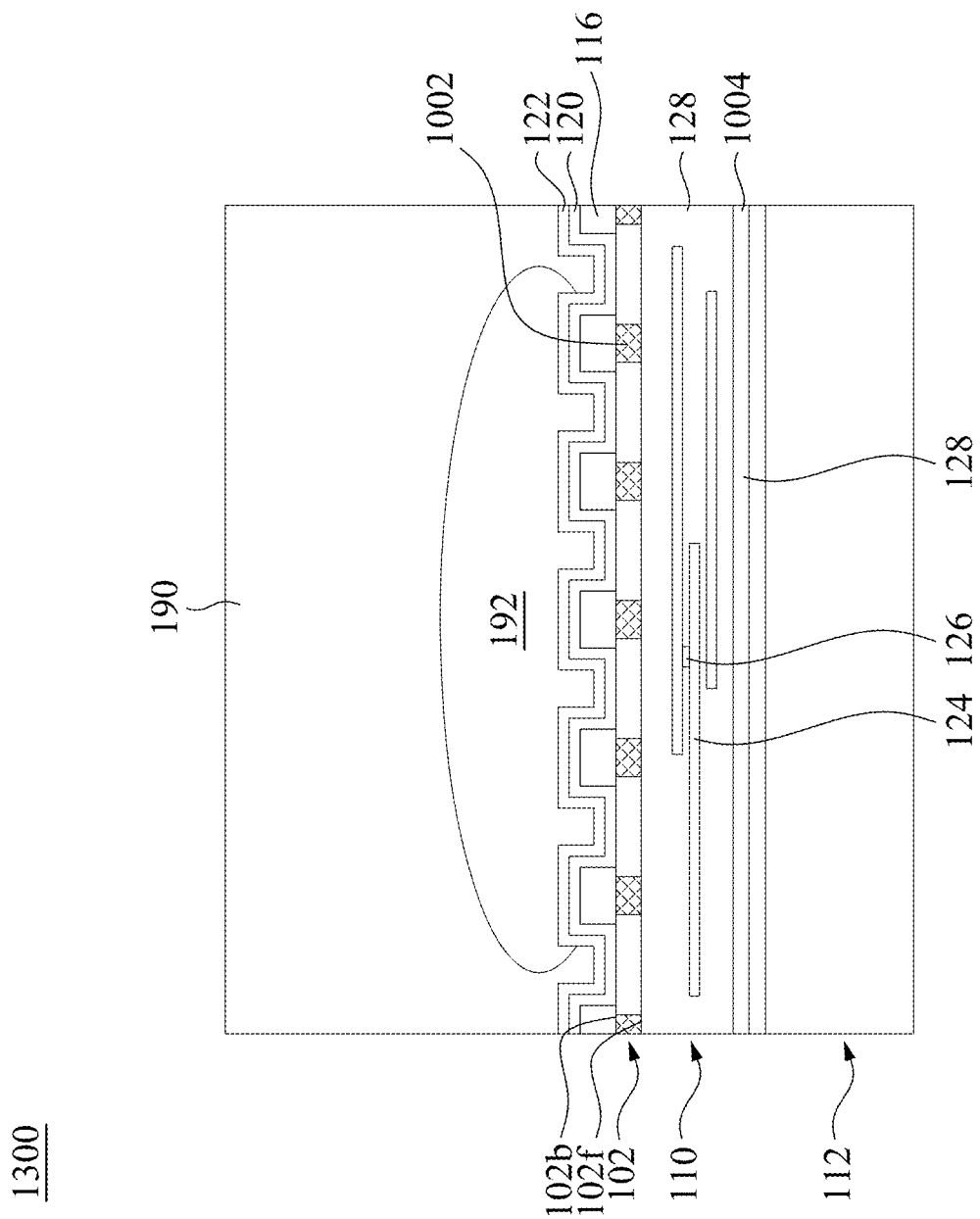
FIG. 13 illustrates a cross-sectional view of another example integrated circuit having the layout of FIG. 10 in accordance with some embodiments.

FIG. 13 illustrates a cross-sectional view of another example integrated circuit 1300 having the layout 1000 of FIG. 10 in accordance with some embodiments, wherein FIG. 13 is a cross-sectional view taken along line B-B' of FIG. 10. The second elongated heaters 1004 in the integrated circuit 1300 is formed in the BEOL interconnect structure 110, not in the active semiconductor layer 102. In some embodiments, the second elongated heaters 1004 include titanium aluminum nitride, platinum, indium tin oxide, titanium nitride, or a combination of the foregoing. In some embodiments, the second elongated heaters 1004 have a thickness in a range from about 5600 angstroms to about 6600 angstroms and a sheet resistance in a range from about 4 ohm/sq to about 6 ohm/sq. In some embodiments, the second elongated heaters 1004 are formed in a metallization layer of the interconnect structure 110 and laterally surrounded by an inter-metal dielectric (IMD) layer of the multi-layer dielectric structure 128. Moreover, other metallization layers including the metal lines 124 and metal vias 126 are formed of a different metal composition (e.g., copper) than that of the second elongated heaters 1004, because these metallization layers including the metal lines 124 and metal vias 126 are not designed for heating.

Figure 14:
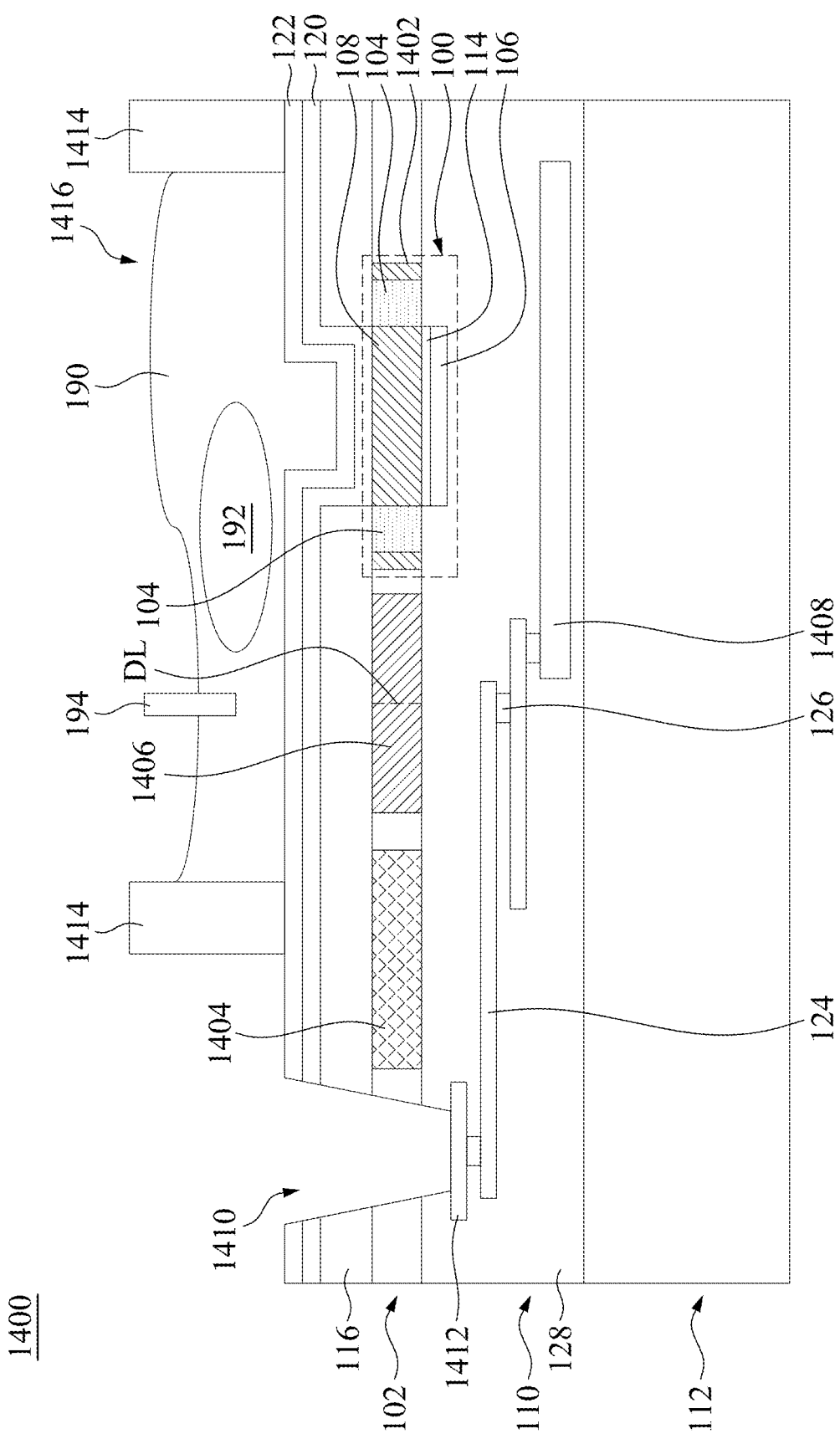
FIG. 14 illustrates a cross-sectional view of an example integrated circuit in accordance with some embodiments of the present disclosure.

FIG. 14 illustrates a cross-sectional view of an example integrated circuit 1400 in accordance with some embodiments of the present disclosure. The integrated circuit 1400 includes a BioFET 100 formed on the active semiconductor layer 102. The BioFET 100 is similar to that described previously with respect to FIG. 1, except that the source/drain regions 104 are formed in a well region 1042 of the active semiconductor layer 102. The well region 1042 has a conductivity type opposite the source/drain regions 104. Moreover, the integrated circuit 1400 includes one or more first heaters 1404 and one or more temperature-sensing devices 1406 formed in the active semiconductor layer 102. The first heater 1404 is a doped region in the active semiconductor layer 102. In some embodiments, the first heater 1404 is formed together with (i.e., simultaneously with) the source/drain regions 104, and thus has the same dopant type and dopant concentration profile as the source/drain regions 104. In some other embodiments, the first heater 1404 is formed together with (i.e., simultaneously with) the well region 1402, and thus has the same dopant type and dopant concentration profile as the well region 1402.

The temperature-sensing device 1406 is a diode formed in the active semiconductor layer 102, and as such the temperature-sensing device 1046 includes at least one P-N junction (as indicated by the dash line DL) forming the diode within the active semiconductor layer 102. In some embodiments, the temperature-sensing device 1046 has a p-type doped region and an n-type doped region to form the P-N junction. In some embodiments where the BioFET 100 is a PFET, the p-type doped region of the temperature-sensing device 1406 is formed together with the source/drain regions 104 of the BioFET 100, and the n-type doped region of the temperature-sensing device 1406 is formed together with the well region 1402. In some embodiments where the BioFET 100 is an NFET, the n-type doped region of the temperature-sensing device 1406 is formed together with the source/drain regions 104 of the BioFET 100, and the p-type doped region of the temperature-sensing device 1406 is formed together with the well region 1402.

The integrated circuit 1400 further includes one or more second heaters 1408 formed in the interconnect structure 110 below the active semiconductor layer 102. In some embodiments, the second heaters 1408 include titanium aluminum nitride, platinum, indium tin oxide, titanium nitride, or a combination of the foregoing. In some embodiments, the second heaters 1408 have a thickness in a range from about 5600 angstroms to about 6600 angstroms and a sheet resistance in a range from about 4 ohm/sq to about 6 ohm/sq. In some embodiments, the second heaters 1408 are formed in a metallization layer of the interconnect structure 110 and laterally surrounded by an inter-metal dielectric (IMD) layer of the multi-layer dielectric structure 128. Moreover, other metallization layers including the metal lines 124 and metal vias 126 are formed of a different metal composition (e.g., copper) than that of the second elongated heaters 1004, because these metallization layers including the metal lines 124 and metal vias 126 are not designed for heating.

The integrated circuit 1400 has a pad opening 1410 extending through the coating of selective binding agent 122, the biosensing film 120, the isolation dielectric layer 160 and the active semiconductor layer 102 to expose a pad structure 1412 formed within the interconnect structure 110. In some embodiments, the pad structure 1412 is formed in a metallization layer of the interconnect structure 110 and laterally surrounded by an inter-metal dielectric (IMD) layer of the multi-layer dielectric structure 128. In some embodiments, a vertical distance from the pad structure 1412 to the active semiconductor layer 102 is less than a vertical distance from the second heater 1408 to the active semiconductor layer 102.

Moreover the integrated circuit 1400 further includes fluid channel walls 1414. The fluid channel walls 1414 laterally define a fluid containment region 1416 over the BioFET 100. The fluid containment region 1416 may be a well or a length of channel bound by fluid channel walls 1414. The fluid channel walls 1414 can be formed of waterproof material(s). In some embodiments, the fluid channel walls 1414 are an elastomer. In some of these embodiments, the elastomer of polydimethylsiloxane (PDMS).

FIGS. 15-22 illustrate cross-sectional views of various intermediate stage of a method for forming the integrated circuit 1400 as illustrated in FIG. 14. Throughout the various views and illustrative embodiments, like reference numbers are used to designate like elements. It is understood that additional operations can be provided before, during, and after the processes shown by FIGS. 15-22, and some of the operations described below can be replaced or eliminated, for additional embodiments of the method. The order of the operations/processes may be interchangeable.

Figure 15:
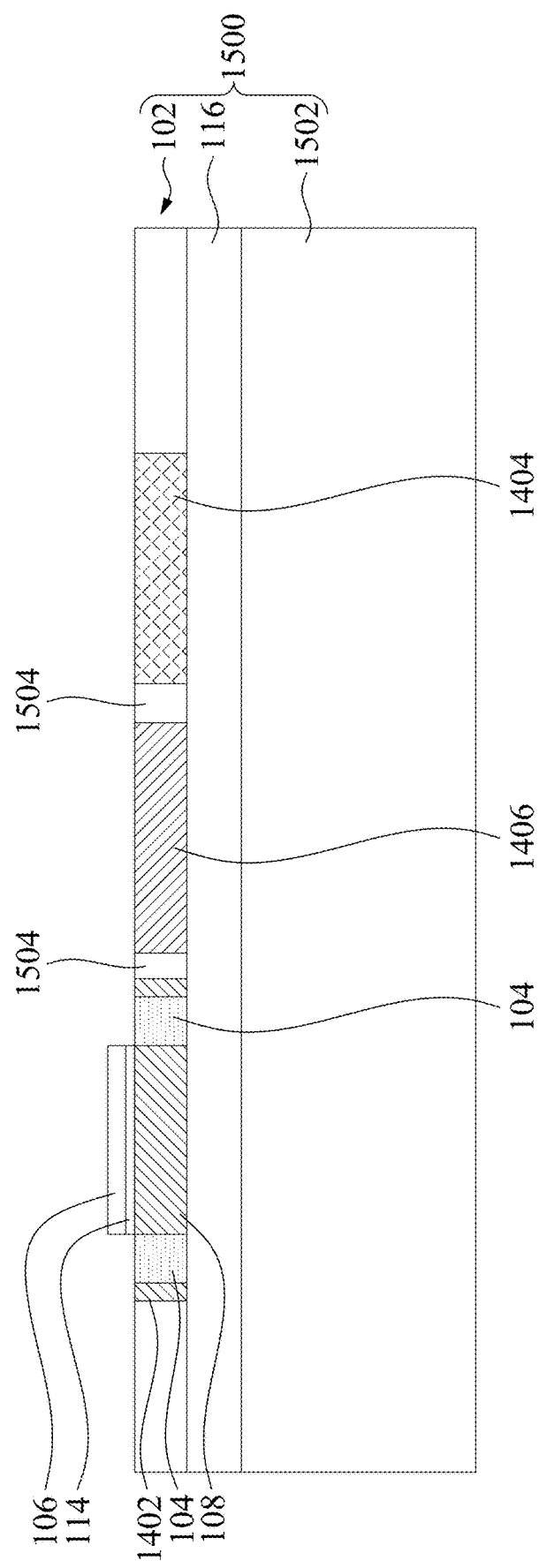
FIGS. 15-22 illustrate cross-sectional views of various intermediate stage of a method for forming the integrated circuit as illustrated in FIG. 14.

As illustrated in FIG. 15, an SOI substrate 1500 is formed. The SOI substrate 1500 comprises a bulk semiconductor substrate 1502 over which an isolation dielectric layer 116 and an active semiconductor layer 102 are stacked. As seen hereafter, the bulk semiconductor substrate 1502 is sacrificial. The bulk semiconductor substrate 1502 and the active semiconductor layer 102 may be, for example, monocrystalline silicon, and/or the isolation dielectric layer 116 may be, for example, silicon dioxide. The SOI substrate 1500 can be formed by any suitable process. In some embodiments, SOI substrate 1500 is formed through separation by implanted oxygen (SIMOX).

After the SOI substrate 1500 is prepared, one or more isolation regions 1504 are optionally formed in the active semiconductor layer 102 of the SOI substrate 1500. In the depicted embodiments, the isolation regions 1504 are formed through the full thickness of the active semiconductor layer 102. In some other embodiments, the isolation regions 1504 are STI regions that do not extend through the full thickness of the active semiconductor layer 102. The isolation regions 1504 extend laterally to enclose subsequently formed BioFETs 100, first heaters 1404 and temperature-sensing devices 1406, so as to provide electrical isolation to these devices.

The process for forming the isolation regions 1504 may comprise, for example, patterning the active semiconductor layer 102 to define one or more trenches corresponding to the isolation regions 1504, subsequently depositing or growing one or more dielectric materials filling the one or more trenches, followed by performing a planarization process (e.g., chemical mechanical polish (CMP)) on the dielectric materials until the active semiconductor layer 102 is exposed. The active semiconductor layer 102 is patterned using suitable photolithography and etching techniques. For example, a photoresist (not shown) may be formed over the active semiconductor layer 102 using a spin-on coating process, followed by patterning the photoresist to forming a plurality of trenches using suitable photolithography techniques, and then the active semiconductor layer 102 is etched using the patterned photoresist as an etch mask until the isolation dielectric layer 116 is exposed. The active semiconductor layer can be etched using, for example, a reactive ion etching (RIE) process or other suitable etching processes. The one or more dielectric materials (e.g., silicon dioxide) may be deposited in the trenches using a high density plasma chemical vapor deposition (HDP-CVD), a low-pressure CVD (LPCVD), sub-atmospheric CVD (SACVD), a flowable CVD (FCVD), spin-on, and/or the like, or a combination thereof.

FIG. 15 also illustrates various doped regions formed in the active semiconductor layer 102. The active semiconductor layer 102 can be doped before or after the isolation regions 1504 are formed. Multiple ion implantation processes are carried out to form the doped regions. In greater detail, a well region 1402 is formed in the active semiconductor layer 102 by a first ion implantation process, and then source/drain regions 104 are formed in the well region 1402 by a second ion implantation process. The source/drain regions 104 are formed with a first doping type (e.g., n-type) and the well region 1402 is formed with a second doping type (e.g., p-type) opposite the first doping type, such that a channel region 108 is formed with a second doping type in the active semiconductor layer 102 between the source/drain regions 104.

In some embodiments where the first heaters 1404 has the same doping type as the source/drain regions 104, the first heaters 1404 can be formed in the active semiconductor layer 102 simultaneously with the source/drain regions 104 using the same ion implantation process. In some embodiments where the first heaters 1404 has the same doping type as the well region 1402, the first heaters 1404 can be formed in the active semiconductor layer 102 simultaneously with the well region 1402 using the same ion implantation process. In some embodiments where the temperature-sensing device 1406 is a diode, a first doped region of the diode 1406 with the same doping type as the source/drain regions 104 can be formed in the active semiconductor layer 102 simultaneously with the source/drain regions 104 using the same ion implantation process, and a second doped region of the diode 1406 with the same doping type as the well region 1402 can be formed in the active semiconductor layer 102 simultaneously with the well region 1402 using the same ion implantation process. In some embodiments, in each ion implantation process photoresist is coated on the active semiconductor layer 102 and patterned on to serve as an implantation mask, which is removed by ashing once the corresponding ion implantation process is complete.

A gate dielectric layer 114 and a gate electrode 106 are formed stacked over the channel region 108, laterally between the source/drain regions 104. In some embodiments, the process for forming the gate dielectric layer 114 and gate electrode 106 comprises sequentially depositing or growing a dielectric layer and a conductive layer stacked over the active semiconductor layer 102. For example, the dielectric and conductive layers may be deposited or grown by, for example, thermal oxidation, electro chemical plating (ECP), vapor deposition, sputtering, or a combination of the foregoing. Further, in some embodiments, the process comprises patterning the dielectric and conductive layers using, for example, photolithography to selectively etch the dielectric and conductive layers respectively into the gate dielectric layer 114 and the gate electrode 106. In some embodiments, the gate dielectric layer 114 includes silicon dioxide, and the gate electrode 106 includes doped polysilicon.

In some embodiments, the ion implantation for forming the source/drain regions 104 are performed after forming the gate dielectric layer 114 and the gate electrode 106, so that a gate stack of gate dielectric layer 114 and the gate electrode 106 can serve as a implantation mask, which allows for the source/drain regions 104 self-aligned to the gate stack.

Figure 16:
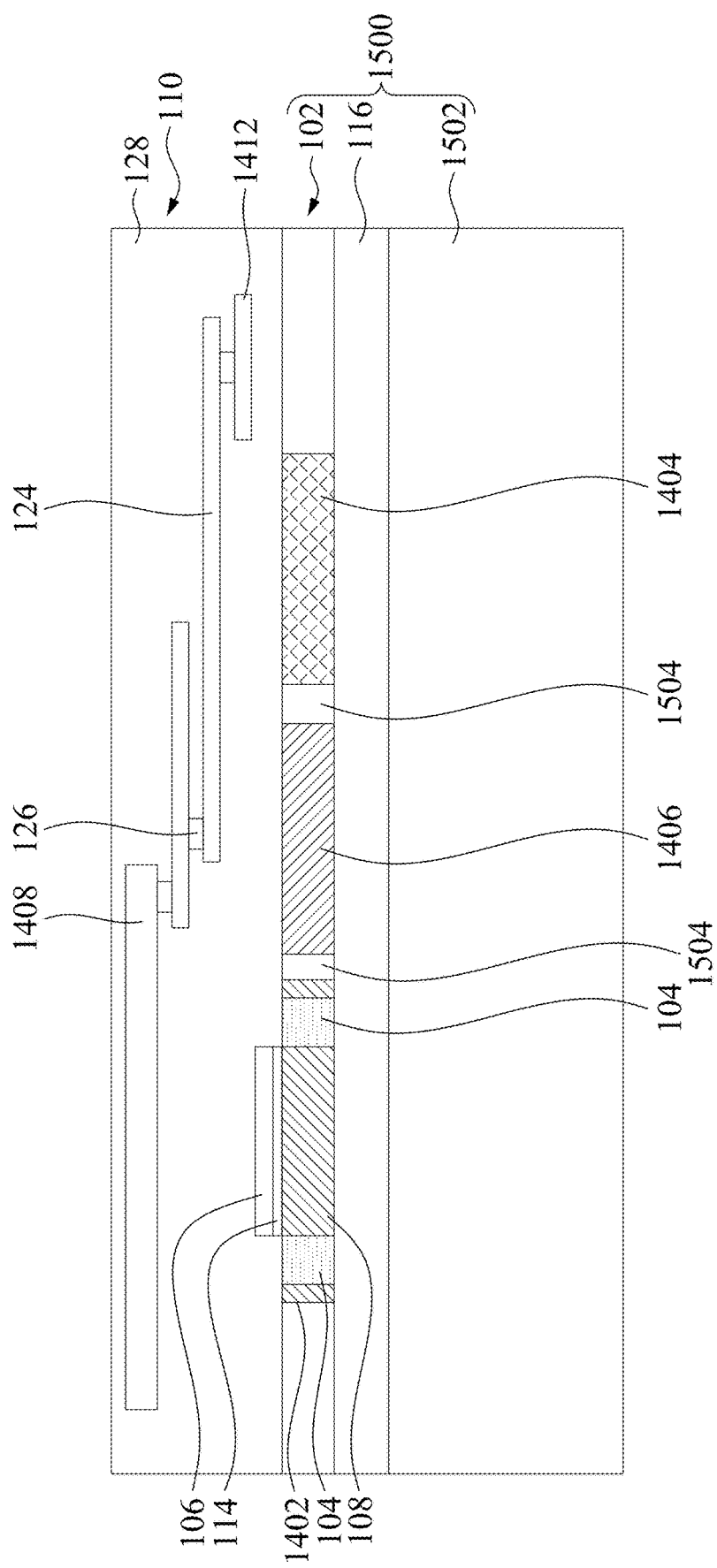

As illustrated in FIG. 16, a BEOL interconnect structure 110 is partially formed over the SOI substrate 1500. The BEOL interconnect structure 110 is formed with metal lines 124 and metal vias 126 alternatingly stacked within a multi-layer dielectric structure 128. The BEOL interconnect structure 110 further include a second heater 1408 and a pad structure 1412 within the multi-layer dielectric structure 128. In some embodiments, the second heater 1408 is formed of a material different from the metal lines 124, metal vias 126 and the pad structure 1412. By way of example and not limitation, the metal lines 124, metal vias 126 and the pad structure 1412 include copper, but the second heater 1408 is free of copper. Instead, the second heater 1408 includes a metal composition with a thermal conductivity lower than copper. For example, the second heater 1408 may include titanium aluminum nitride, platinum, indium tin oxide, titanium nitride, or a combination of the foregoing. The reduced thermal conductivity of the second heater 1408 is helpful in temperature increase in a shorter time. In some embodiments, the pad structure 1412 has a larger plan view area (or larger top view area) than the metal lines 124 and vias 126, which in turn helps for wire bonding on the pad structure 1412.

The second heater 1408, metal lines 124, metal vias 126 and pad structure 1412 may be, for example, formed by a single-damascene-like process or a dual-damascene-like process. A single-damascene-like or dual-damascene-like process is a single-damascene or dual-damascene process that is not restricted to copper. By way of example, a first inter-metal dielectric (IMD) layer is formed over the gate electrode 106 and then patterned to form an opening in the first IMD layer, one or more metals (e.g., copper) is then deposited to overfill the opening in the first IMD layer, followed by performing a CMP process on the one or more metals until the first IMD layer is exposed, resulting in the pad structure 1412 inlaid in the first IMD layer. Thereafter, a second IMD layer is formed over the first IMD layer and patterned to form via openings in the second IMD layer, one or more metals (e.g., copper) is then deposited to overfill the via openings in the second IMD layer, followed by performing a CMP process on the one or more metals until the second IMD layer is exposed, resulting in the metal vias 126 inlaid in the second IMD layer. Afterwards, a third IMD layer is formed over the second IMD layer and patterned to form trenches laterally extending in the third IMD layer, one or more metals (e.g., copper) is then deposited to overfill the trenches in the third IMD layer, followed by performing a CMP process on the one or more metals until the third IMD layer is exposed, resulting in the metal lines 124 inlaid in the third IMD layer.

The second heater 1408 is formed in a manner similar to that of the metal lines 124. By way of example and not limitation, an upper IMD layer is formed over a lower IMD layer having metal vias 126 (both the upper and lower IMD layers are higher than the third IMD layer as described above), the upper IMD layer is then patterned to form trenches laterally extending in the upper IMD layer, one or more non-copper metals (e.g., titanium aluminum nitride) is then deposited to overfill the trenches in the upper IMD layer, followed by performing a CMP process on the one or more metals until the upper IMD layer is exposed, resulting in the second heater 1408 inlaid in the upper IMD layer. Another IMD layer is then formed over the second heater 1408, and these IMD layers are in combination referred to as a multi-layer dielectric structure 128. In some embodiments, the second heater 1408 includes metal lines laterally extending within the multi-layer dielectric structure 128, and the metal lines of the second heater 1408 may have a line width less than line widths of the metal lines 124, which in turn results in an increased thermal resistance for the second heater 1408, thus facilitating temperature increase in a shorter time.

Figure 17:
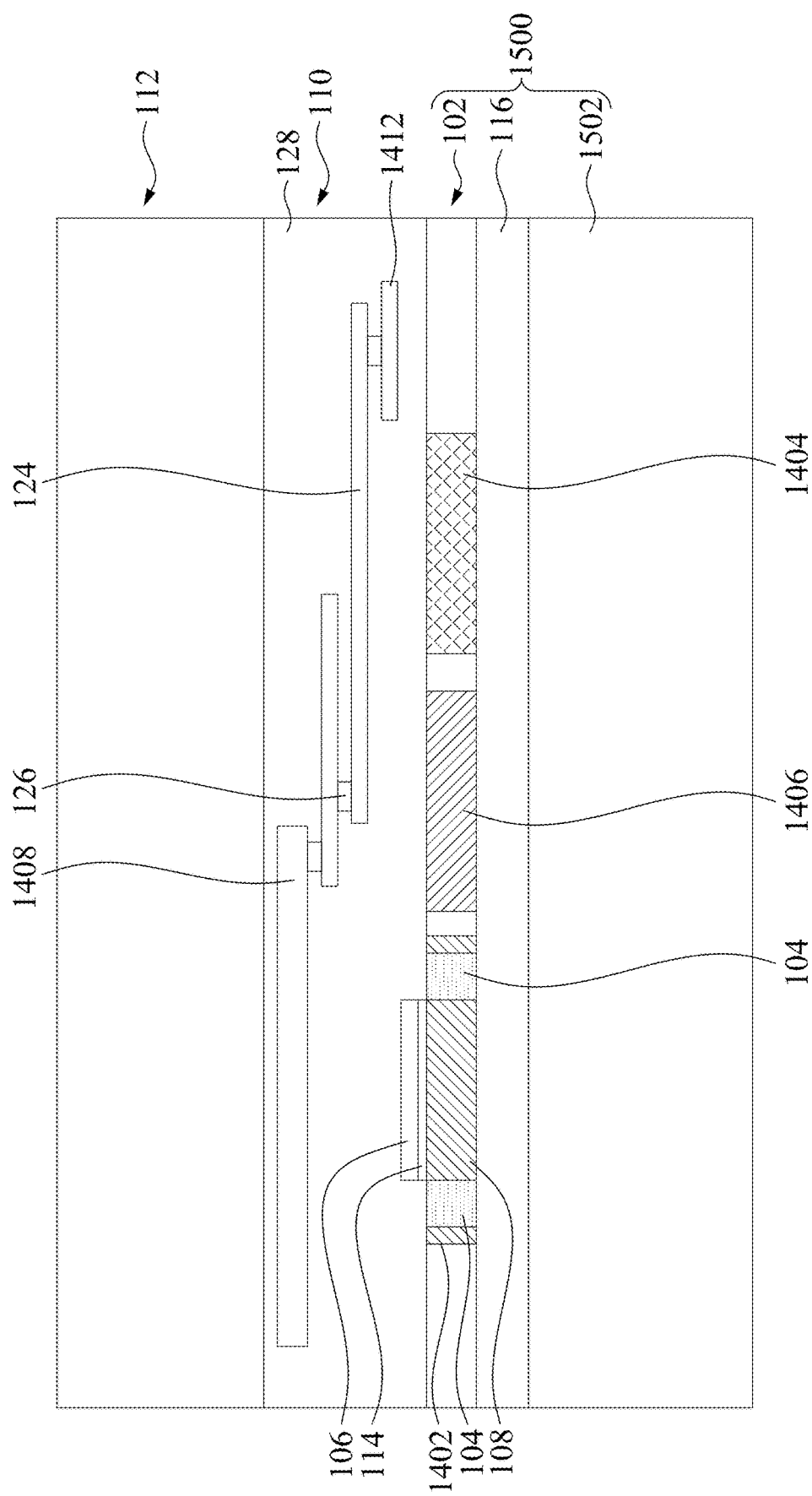

As illustrated in a cross-sectional view of FIG. 17, a carrier substrate 112 is bonded to the SOI substrate 1500 through the BEOL interconnect structure 110. For example, the carrier substrate 112 may be bonded to the BEOL interconnect structure 110 by a fusion bonding process, such as a hydrophilic fusion bonding process.

Figure 18:
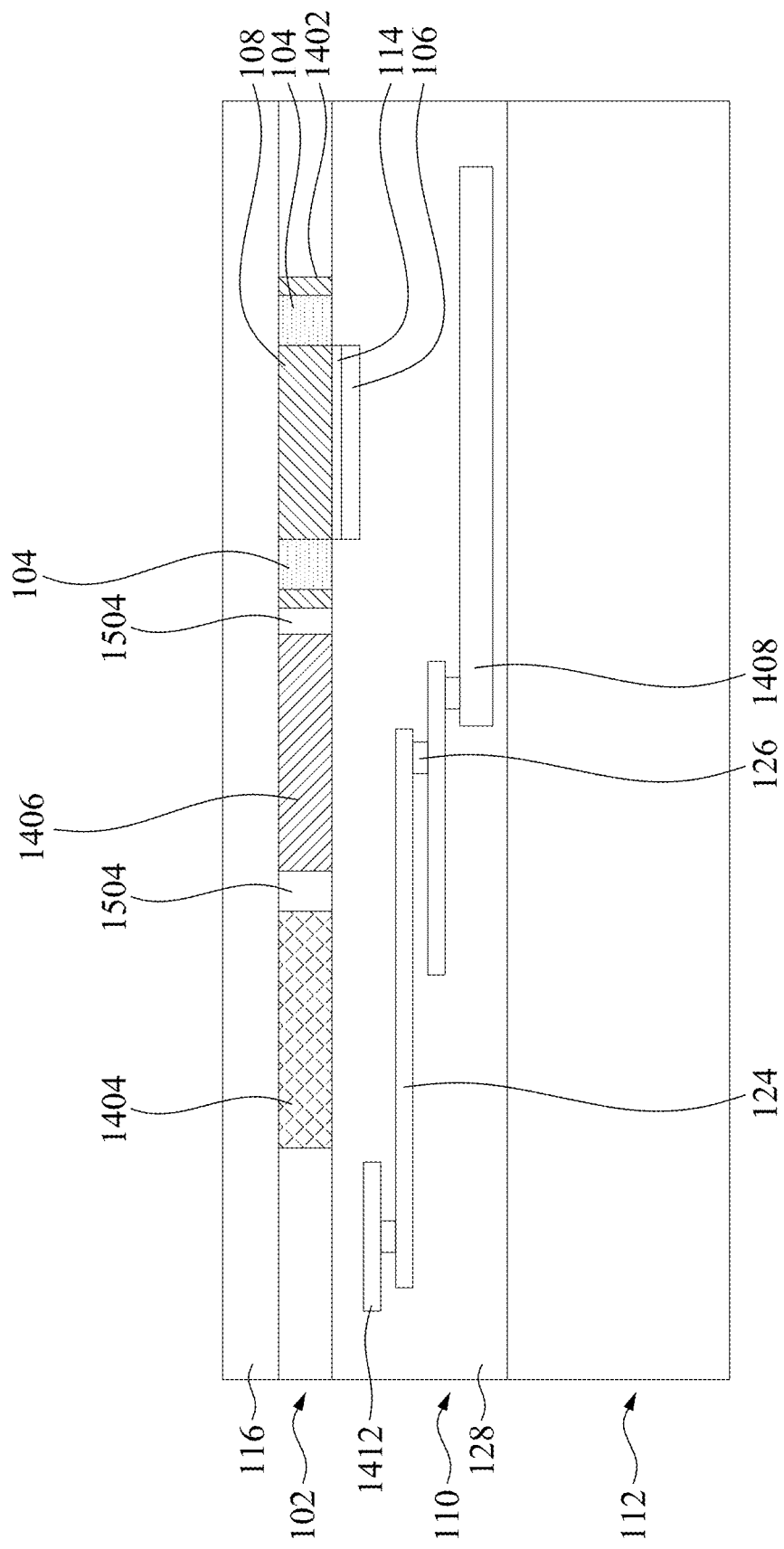

As illustrated in a cross-sectional view of FIG. 18, the structure of FIG. 17 is flipped vertically and the SOI substrate 1500 is thinned to remove the bulk semiconductor substrate 1502 (see, e.g., FIG. 17). In some embodiments, the bulk semiconductor substrate 1502 is removed by grinding, CMP, etching back, or a combination of the foregoing. The isolation dielectric layer (e.g., BOX layer) 116 remains after removing the bulk semiconductor substrate 1502.

Figure 19:
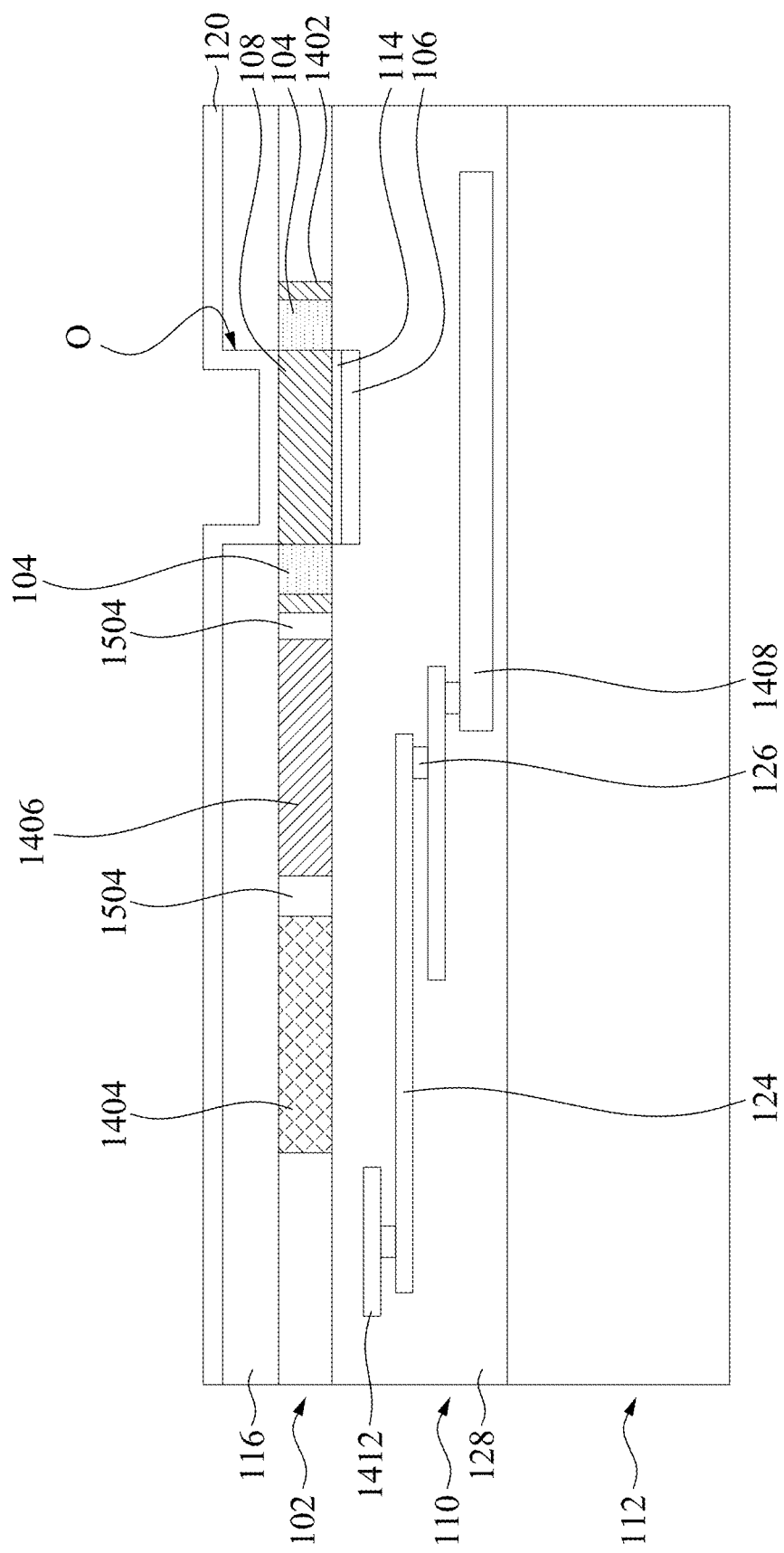

As illustrated in a cross-sectional view of FIG. 19, the isolation dielectric layer 116 is patterned to form a sensing well O over the channel region 108 and laterally between the source/drain regions 104. The isolation dielectric layer 116 is patterned using suitable photolithography and etching techniques. For example, a photoresist (not shown) may be formed over the isolation dielectric layer 116 using a spin-on coating process, followed by patterning the photoresist to forming an opening using suitable photolithography techniques, and then the isolation dielectric layer 116 is etched using the patterned photoresist as an etch mask until the channel region 108 is exposed. Example etchant for etching the isolation dielectric layer 116 includes hydrofluoric acid, if the isolation dielectric layer 116 is silicon dioxide.

Once the sensing well O is formed, a biosensing film 120 is formed lining the sensing well O. In some embodiments, the biosensing film 120 is also formed covering the isolation dielectric layer 116. The biosensing film 120 may be deposited using, for example, vapor deposition, sputtering, atomic layer deposition (ALD), or a combination of the foregoing. Moreover, the biosensing film 120 includes, for example, include $HfO_2$, $SiO_2$, $Si_3N_4$, $Al_2O_3$, $Ta_2O_5$ or combinations thereof.

Figure 20:
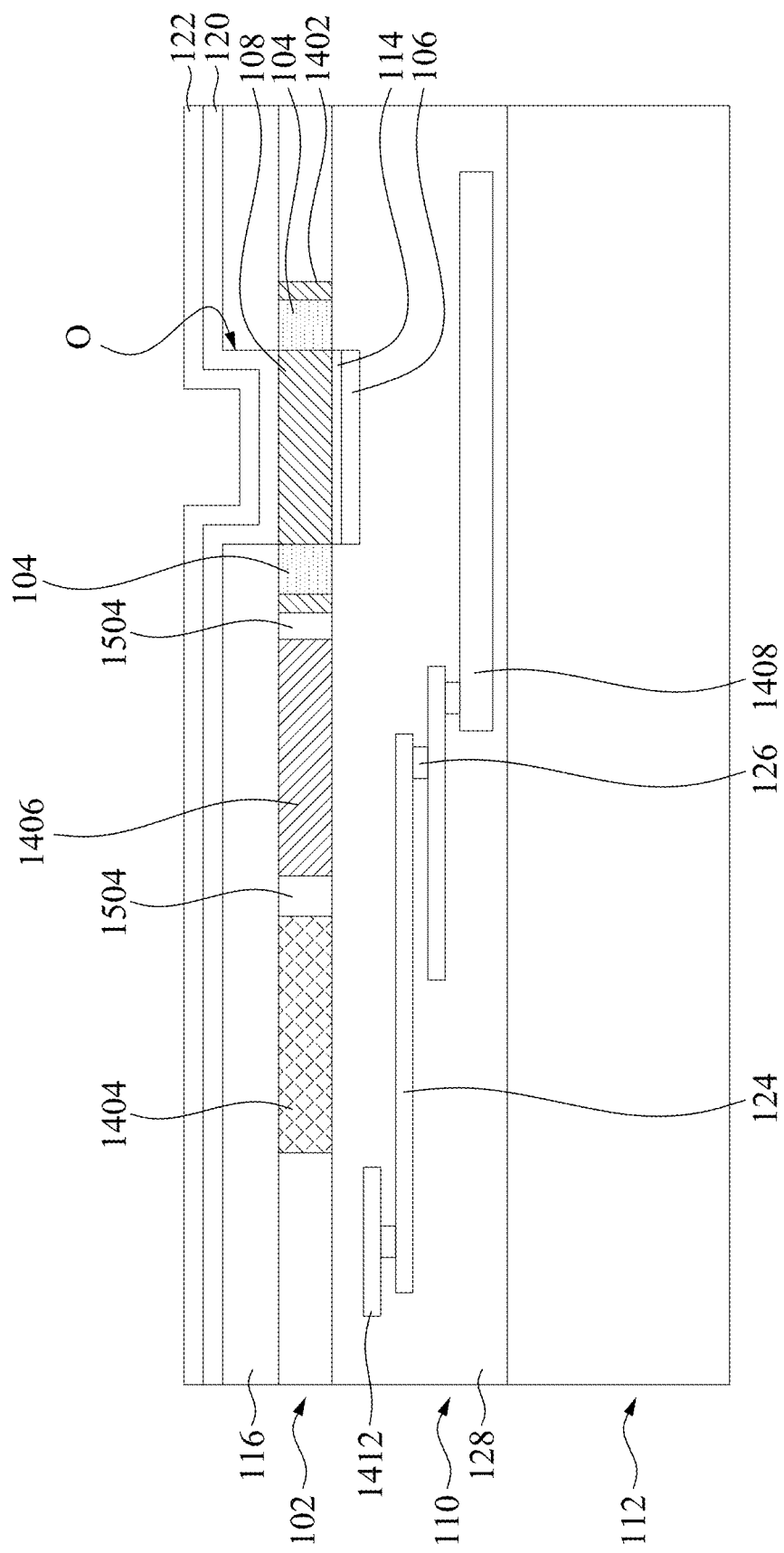

As illustrated in a cross-sectional view of FIG. 20, the biosensing film 120 is coated with a selective binding agent 122. Coating the biosensing film 120 with the selective binding agent 122 includes, but is not limited to, immersing the wafer having the structure of FIG. 19 in a selective binding agent bath at a suitable temperature (e.g., from about 25 degrees Celsius to about 300 degrees Celsius) for a suitable time duration (e.g., from about 5 mins to about 10 hrs) that is sufficient to allow the selective binding agent 122 to be attached to the biosensing film 120, thus resulting in a thin film coating of the selective binding agent 122 in contact with the selective binding agent 122. In some embodiments, the thin film coating of selective binding agent 122 is porous, which allows for the biosensing film 120 to be in contact with the cardiac-cell-containing fluid. In some embodiments, the binding agent 122 includes silane coupling agents that are compounds whose molecules contain functional groups that bond with both organic and inorganic materials. A silane agent acts as a sort of intermediary which bonds organic materials to inorganic materials. The silane coupling agent may include, by way of example and not limitation, silane having vinyl functional group (e.g., Vinyltrimethoxysilane (($CH_3O)_3SiCH=CH_2$), Vinyltriethoxysilane (($C_2H_5O)_3SiCH=CH_2$) or the like), silane having epoxy functional group (e.g., 2-(3, 4 epoxy-cyclohexyl) ethyltrimethoxysilane, 3-Glycidoxypropyl methyldimethoxysilane, 3-Glycidoxypropyl trimethoxysilane, 3-Glycidoxypropyl methyldiethoxysilane, 3-Glycidoxypropyl triethoxysilane or the like), silane having styryl functional group (e.g., p-Styryltrimethoxysilane or the like), silane having methacryloxy functional group (e.g., 3-Methacryloxypropyl methyldimethoxysilane, 3-Methacryloxypropyl trimethoxysilane, 3-Methacryloxypropyl methyldiethoxysilane, 3-Methacryloxypropyl triethoxysilane or the like), silane having acryloxy functional group (e.g., 3-Acryloxypropyl trimethoxysilnae or the like), silane having amino functional group (e.g., N-2-(Aminoethyl)-3-amonopropylmethyldimethoxysilane, N-2-(Aminoethyl)-3-aminopropyltrimethoxysilane, 3-Aminopropyltrimethoxysilane, 3-Aminopropyltriethoxysilane, 3-Triethoxysilyl-N-(1, 3 dimethy-butylidene) propylamine, N-Pheny-3-aminopropyltrimethoxysilane, N-(Vinylbenzyl)-2-aminoethyl-3-aminopropyltrimethoxysilane hydrochloride or the like), silane having ureide functional group (e.g., 3-Ureidopropyltrialkoxysilane or the like), silane having isocyanate functional group (e.g., 3-Isocyanatepropyltriethoxysilane or the like), silane having isocyanurate functional group (e.g., Tris-(trimethoxysilylpropyl)isocyanurate or the like), silane having mercapto functional group (e.g., 3-Mercaptopropylmethyldimethoxysilane, 3-Mercaptopropyltrimethoxysilane or the like) or silane having other suitable functional groups. In some embodiments, the selective binding agent 122 for selectively binding with the cardiac cell 192 includes, for example, collagen, laminin, fibronectin, and mucopolysaccharides, heparin sulfate, hyaluronidate, chondroitin sulfate, the like, or combinations thereof.

In some embodiments, an additional surface treatment is performed on the biosensing film 120 before forming the coating of selective binding agent 122. The surface treatment includes, for example, a plasma treatment and/or a liquid-phase chemistry treatment that is capable of improving hydrophilicity of the biosensing film 120. For example, the biosensing film 120 may undergo $O_2$ or $O_3$ plasma treatment before forming the coating of selective binding agent 122, so as to improve hydrophilicity of the biosensing film 120. The biosensing film 120 with improved hydrophilicity will be helpful in attachment to the cardiac cell, thus improving the detection and/or monitoring on the cardiac cell.

Figure 21:
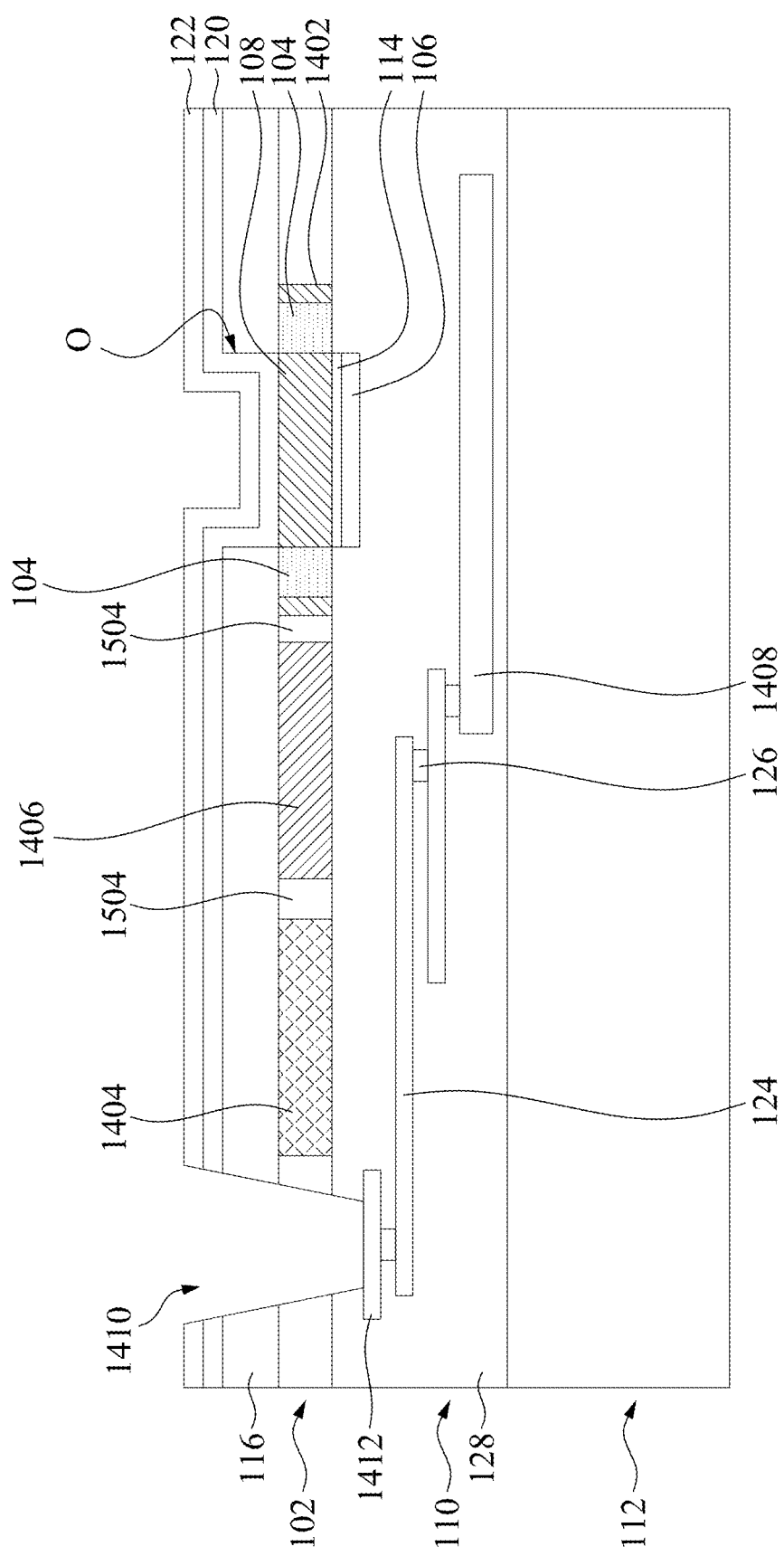

As illustrated in a cross-sectional view of FIG. 21, in some embodiments, an etching process is performed into the coating of selective binding agent 122, the biosensing film 120, the isolation dielectric layer 116, the active semiconductor layer 102, the multi-layer dielectric structure 128 to form a pad opening 1410 exposing the pad structure 1412 of the BEOL interconnect structure 110. The process for performing the etching may comprise, for example, coating a photoresist over the coating of selective binding agent 122 and patterning the photoresist using photolithography, such that the patterned photoresist has an opening corresponding to the pad opening 1410. With the patterned photoresist in place, the etching process may comprise, for example, applying one or more etchants to the coating of selective binding agent 122, the biosensing film 120, the isolation dielectric layer 116, the active semiconductor layer 102, the multi-layer dielectric structure 128, and subsequently stripping the patterned photoresist by ashing.

Figure 22:
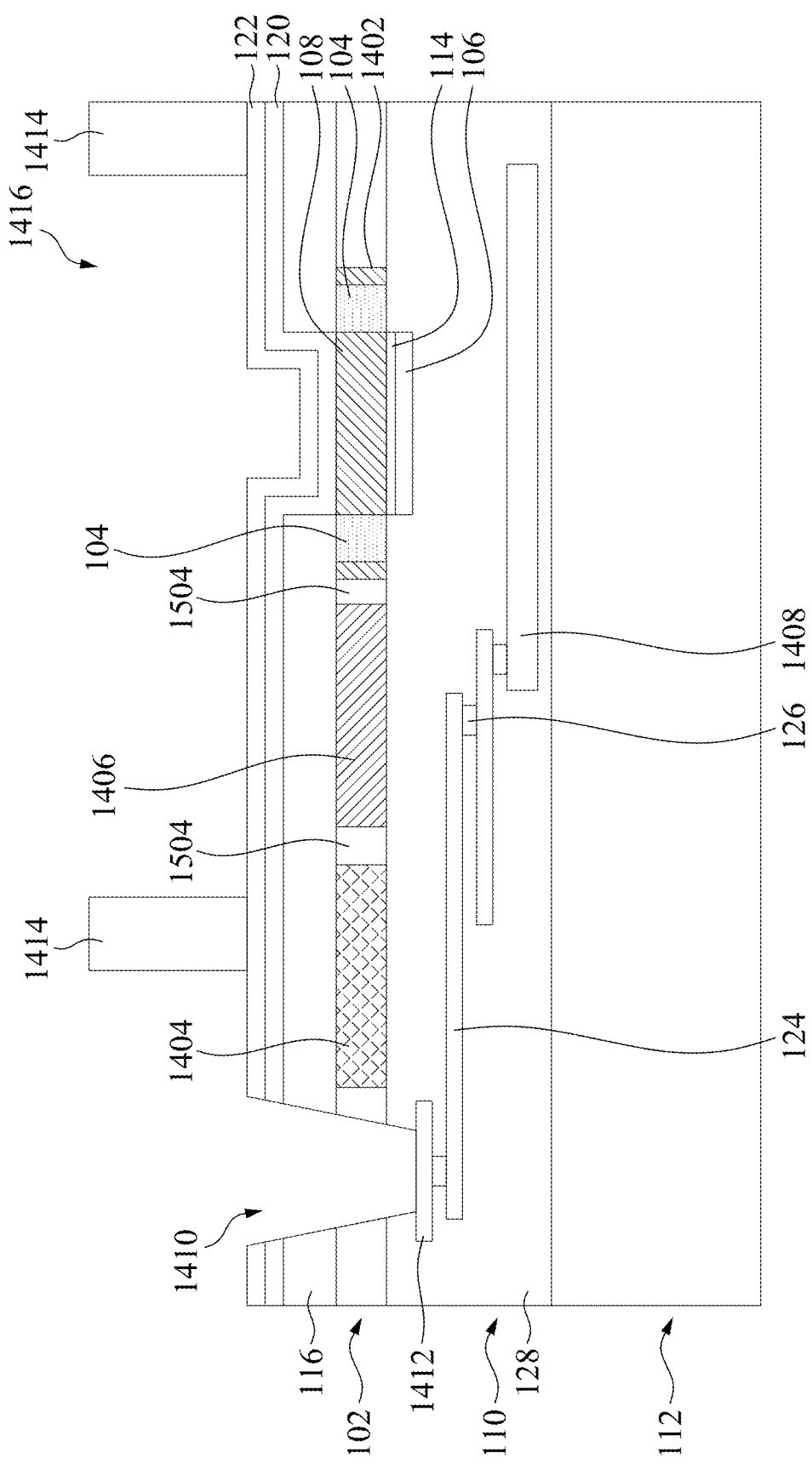

As illustrated by a cross-sectional view of FIG. 22, fluid channel walls 1414 are formed over the coating of selective binding agent 122 to define a fluid containment region 1416 over the sensing well O. In some embodiments, the fluid channel walls 1414 include an elastomer. In some embodiments, the elastomer is polydimethylsiloxane (PDMS). In some embodiments, a layer of elastomer is patterned and then attached to the structure of FIG. 21 to form fluid channel walls 1414. In some embodiments, the material of fluid channel walls 1414 is first deposited and then pattern on the structure of FIG. 21.

Figure 23:
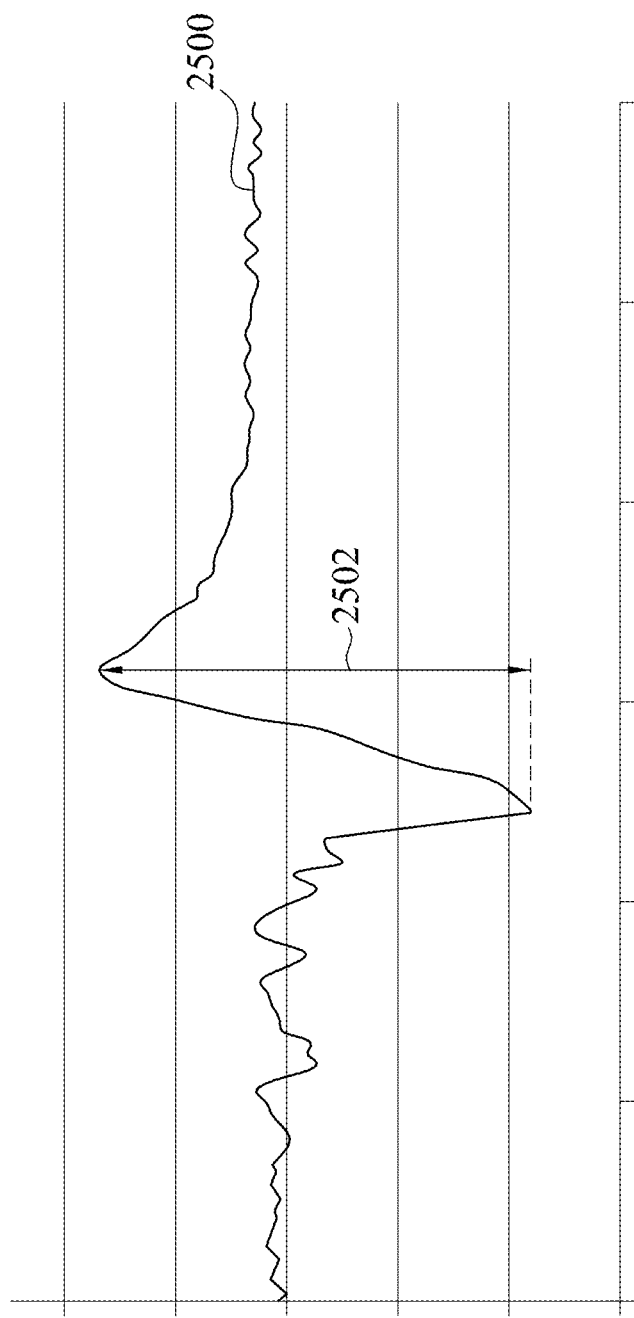
FIG. 23 is a chart illustrating an experimental result of a cardiac cell measured using an integrated circuit having BioFETs in some embodiments of the present disclosure.

FIG. 23 is a chart illustrating an experimental result of a cardiac cell measured using an integrated circuit having BioFETs 100 as discussed above. The experimental result includes a time domain signal 2500 measured from a cardiac cell using the BioFETs 100. The time domain signal 2500 indicates that beating pulse 2502 is greater than about 4 µA. The time domain signal 2500 detected by the BioFETs 100 is similar to a normal cardiac cycle, and thus the experimental result shows that the integrated circuit having BioFETs 100 can serve as a promising candidate for monitoring beating of cardiac cells.

Figure 24:
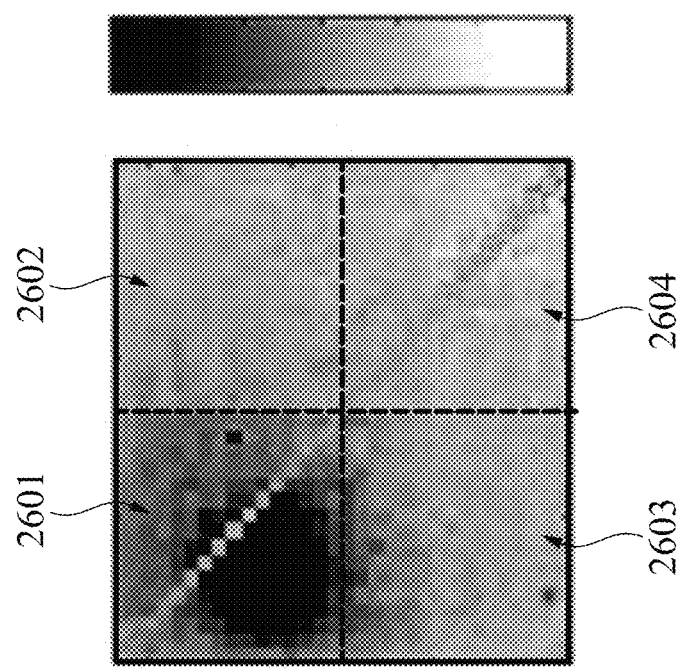
FIG. 24 is a 2D electrical image of a cardiac cell obtained using an integrated circuit having an array of BioFETs in some embodiments of the present disclosure.

FIG. 24 is a 2D electrical image of a cardiac cell obtained using an integrated circuit having an array of BioFETs 100 as discussed above. The array of BioFETs 100 includes sensing pixels 2601, 2602, 2603 and 2604. In the experiment a cardiac cell is placed on the sensing pixel 2601 and no cardiac cell is placed on the sensing pixels 2602-2604, and the 2D electrical image clearly indicates that a cardiac cell in on the sensing pixel 2601 and no cardiac cell is placed on the sensing pixels 2602-2604. Moreover, the 2D electrical image properly reflects the 2D image profile of the cardiac cell. This experimental result shows that the integrated circuit having BioFETs 100 can serve as a promising candidate for generating a 2D image of one or more cardiac cells.

Based on the above discussions, it can be seen that the present disclosure offers advantages. It is understood, however, that other embodiments may offer additional advantages, and not all advantages are necessarily disclosed herein, and that no particular advantage is required for all embodiments. One advantage is that cardiac cells can be detected, measured and/or monitored using an IC having BioFETs. Another advantage is that the coating of selective binding agent on the biosensing film aids in binding the cardiac cell to the biosensing film, thus improving the accuracy of the measurement result of cardiac cell.

In some embodiments, an IC includes a source region and a drain region in a semiconductor layer. A channel region is laterally between the source region and the drain region. A sensing well is on a back surface of the semiconductor layer and over the channel region. An interconnect structure is on a front surface of the semiconductor layer opposite the back surface of the semiconductor layer. A biosensing film lines the sensing well and contacts a bottom surface of the sensing well that is defined by the semiconductor layer. A coating of selective binding agent is over the biosensing film and configured to bind with a cardiac cell.

In some embodiments, an IC includes a semiconductor substrate having a source region and a drain region. A sensing well is on a back surface of the semiconductor substrate. A biosensing film lines the sensing well and contacts the back surface of the semiconductor substrate. A biological material coating layer is over the biosensing film. A first heater is in the semiconductor substrate and laterally spaced from the source region and the drain region. The first heater vertically overlaps with the biological material coating layer.

In some embodiments, a method includes forming a semiconductor-on-insulator (SOI) substrate comprising a semiconductor substrate, a sacrificial substrate and a dielectric layer between the semiconductor substrate and the sacrificial substrate; forming source/drain regions in the semiconductor substrate; forming a back-end-of-line (BEOL) interconnect structure on a first side of the semiconductor substrate; bonding a carrier substrate to the semiconductor substrate through the BEOL interconnect structure; after bonding the carrier substrate to the semiconductor substrate; thinning the SOI substrate to remove the sacrificial substrate and to expose the dielectric layer; etching the dielectric layer until a second side of the semiconductor substrate is exposed, resulting in a sensing well extending through the dielectric layer and laterally between the source/drain regions; forming a biosensing film lining the sensing well; and immersing the biosensing film in a biological material bath until the biosensing film is coated with a biological material layer.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. An integrated circuit (IC), comprising:
a source region and a drain region in a semiconductor layer;
a channel region laterally between the source region and the drain region;
a sensing well on a back surface of the semiconductor layer and over the channel region, wherein a bottom surface of the sensing well is defined by the semiconductor layer;
an interconnect structure on a front surface of the semiconductor layer opposite the back surface of the semiconductor layer;
a biosensing film lining the sensing well and contacting the bottom surface of the sensing well;
a coating of selective binding agent over the biosensing film and configured to bind with a cardiac cell;
a plurality of first elongated heaters in the semiconductor layer; and
a plurality of fluid channel walls formed over the coating of the selective binding agent, wherein one of the fluid channel walls forms a horizontal interface with the coating of the selective binding agent, and an entirety of the horizontal interface vertically overlaps with one of the plurality of first elongated heaters in the semiconductor layer.

2. The IC of claim 1, wherein the coating of selective binding agent comprises collagen, laminin, fibronectin, mucopolysaccharides, heparin sulfate, hyaluronidate, and chondroitin sulfate.

3. The IC of claim 1, wherein the coating of selective binding agent is porous.

4. The IC of claim 1, further comprising:
at least one second elongated heater within the interconnect structure.

5. The IC of claim 4, wherein the second elongated heater is formed of a material different from a material of metal lines and metal vias of the interconnect structure.

6. The IC of claim 4, wherein the second elongated heater is free of copper.

7. The IC of claim 4, wherein a plurality of the second elongated heaters form parallel elongate patterns from a top view.

8. The IC of claim 7,
wherein the first elongated heaters form elongated patterns crossing the elongated patterns formed from the second elongated heaters from the top view.

9. The IC of claim 1, further comprising a temperature-sensing device in the semiconductor layer.

10. The IC of claim 9, wherein the temperature-sensing device is a diode.

11. The IC of claim 1, wherein the plurality of first elongated heaters are doped silicon regions in the semiconductor layer.

12. An integrated circuit (IC), comprising:
a semiconductor substrate having a source region and a drain region;
a sensing well on a back surface of the semiconductor substrate;
a biosensing film lining the sensing well and contacting the back surface of the semiconductor substrate;
a biological material coating layer over the biosensing film;
a first heater in the semiconductor substrate and laterally spaced from the source region and the drain region, the first heater vertically overlapping with the biological material coating layer; and
a plurality of fluid channel walls formed over the biological material coating layer, wherein one of the fluid channel walls forms a horizontal interface with the biological material coating layer, and an entirety of the horizontal interface vertically overlaps with the first heater in the semiconductor substrate.

13. The IC of claim 12, further comprising:
a temperature-sensing device in the semiconductor substrate and vertically overlapping with the biological material coating layer.

14. The IC of claim 13, further comprising:
an isolation dielectric region in the semiconductor substrate and laterally between the first heater and the temperature-sensing device.

15. The IC of claim 12, further comprising:
a gate electrode on a front surface of the semiconductor substrate and laterally between the source region and the drain region; and
a second heater on the front surface of the semiconductor substrate, wherein the second heater is formed of a same material as the gate electrode.

16. The IC of claim 15, wherein the first heater is a doped silicon region in the semiconductor substrate, and the second heater is polysilicon.

17. An IC comprising:
a semiconductor substrate having a source region and a drain region;
a sensing well on a back surface of the semiconductor substrate;
a biosensing film lining the sensing well and contacting the back surface of the semiconductor substrate;

a coating of selective binding agent over the biosensing film;

a plurality of fluid channel walls over the coating of selective binding agent and defining a fluid containment region over the sensing well; and a plurality of first elongated heaters in the semiconductor substrate, wherein one of the fluid channel walls forms a horizontal interface with the coating of the selective binding agent, and an entirety of the horizontal interface vertically overlaps with one of the plurality of first elongated heaters in the semiconductor substrate.

18. The IC of claim 17, wherein the sensing well vertically overlaps a channel region in the semiconductor substrate between the source region and the drain region.

19. The IC of claim 18, wherein the channel region extends through a full thickness of a semiconductor layer in the semiconductor substrate.

20. The IC of claim 17, wherein the coating of selective binding agent comprises collagen, laminin, fibronectin, mucopolysaccharides, heparin sulfate, hyaluronidate, and chondroitin sulfate.

* * * * *